United States Patent [19]

Ohyama et al.

[11] Patent Number: 4,512,989
[45] Date of Patent: * Apr. 23, 1985

[54] 1,2,4-TRIAZOLE DERIVATIVES AND FUNGICIDAL COMPOSITION CONTAINING THE SAME

[75] Inventors: Hiroshi Ohyama, Chigasaki; Ken Morita, Hiratsuka; Takuo Wada, Hatano; Masahiko Miyahara, Atsugi, all of Japan

[73] Assignee: Hokko Chemical Industry Co., Ltd., Tokyo, Japan

[*] Notice: The portion of the term of this patent subsequent to Jul. 5, 2000 has been disclaimed.

[21] Appl. No.: 433,623

[22] Filed: Oct. 8, 1982

[30] Foreign Application Priority Data

Oct. 15, 1981 [JP] Japan .................. 56-163409

[51] Int. Cl.³ .............. A01N 43/64; A01N 55/02; C07D 249/08; C07F 1/08
[52] U.S. Cl. .................. 514/383; 548/101; 548/262
[58] Field of Search .......... 548/101, 262; 424/245, 424/269

[56] References Cited

U.S. PATENT DOCUMENTS

| | | | |
|---|---|---|---|
| 3,993,469 | 11/1976 | Regel et al. | 544/370 |
| 4,118,487 | 10/1978 | Regel et al. | 424/269 |
| 4,208,411 | 6/1980 | Ikura et al. | 424/245 |
| 4,391,804 | 7/1983 | Ohyama et al. | 548/341 |

Primary Examiner—Alton D. Rollins
Attorney, Agent, or Firm—Larson and Taylor

[57] ABSTRACT

A new 1,2,4-triazole compound is now provided, which is represented by the general formula

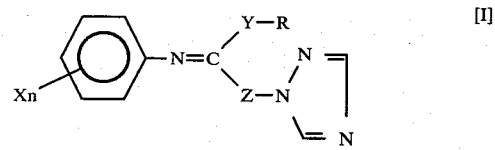

wherein X may be the same or different and denotes a halogen atom, a ($C_1$–$C_4$)alkyl group, a ($C_1$–$C_4$)alkoxyl group, a ($C_1$–$C_4$)alkylthio group, a ($C_1$–$C_4$) alkylsulfinyl group, a ($C_1$–$C_4$)alkylsulfonyl group, a trifluoromethyl group, a nitro group or a cyano group;

n is an integer of 0 to 5;

R denotes a ($C_1$–$C_4$)alkyl group, a ($C_2$–$C_4$)alkenyl group, a ($C_2$–$C_4$)alkynyl group, a ($C_1$–$C_4$)alkoxy-($C_1$–$C_4$)alkyl group, a ($C_1$–$C_4$)alkylthio-($C_1$–$C_4$)alkyl group, a ($C_3$–$C_6$)cycloalkyl group, a ($C_3$–$C_6$)cycloalkyl-($C_1$–$C_4$)alkyl group, a substituted or unsubstituted phenyl group, or a phenyl($C_1$–$C_4$)alkyl group of which the phenyl may optionally bear up to three substituents, Y denotes an oxygen atom or a sulfur atom; and Z denotes a linear or branched ($C_1$–$C_6$)alkylene group, or a salt of said 1,2,4-triazole derivative.

The new 1,2,4-triazole compound and its salt show a usefully high fungicidal activity against a wide variety of fungi which infest crop plants. The new 1,2,4-triazole compound and its salt may be useful as fungicidal agent of agricultural and horticultural usages.

12 Claims, No Drawings

1,2,4-TRIAZOLE DERIVATIVES AND FUNGICIDAL COMPOSITION CONTAINING THE SAME

BACKGROUND OF THE INVENTION

1. Field of the Invention

This invention relates to new 1,2,4-triazole derivatives and their salts which exhibit a high fungicidal activity against a wide variety of fungi which usually infest crop plants in the agricultural field. This invention also relates to the use of these new 1,2,4-triazole derivatives or their salts as fungicidal agent of agricultural and horticultural utilities.

2. Description of the Prior Art

Many kinds of fungicidal compounds are known, and among of them, some 1,2,4-triazole derivatives are known to have the fungicidal activity. For instance, from Japanese patent application unexamined prepublication "Kokai" No. Sho 52-27767 (published on Mar. 2nd, 1977, corresponding to U.K. patent applications No. 35208/75, No. 37241/75, No. 37244/75, No. 51039/75, No. 671/76 and No. 27649/76), it is known that an ester, anilide or imine derivative of a 1,2,4-triazol-1-yl-alkanoic acid represented by the general formula

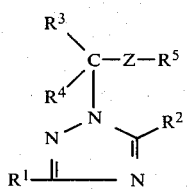

wherein $R^1$, $R^2$ and $R^3$ are each a hydrogen atom; $R^4$ are each a hydrogen atom or a substituted or unsubstituted hydrocarbyl group; and $R^5$ is a hydroxyl group, a substituted or unsubstituted hydrocarbyloxy group, or a substituted or unsubstituted amino group, a hydrazino group, or a substituted or unsubstituted hydrocarbyl group; and Z is a group >C=O or >C=NH is useful as fungicidal agent of agricultural and horticultural utilities. However, these known 1,2,4-triazole derivatives have not always satisfactorily high fungicidal activity against a wide variety of the fungal pests.

SUMMARY OF THE INVENTION

An object of this invention is to provide a new 1,2,4-triazole derivative which exhibits a satisfactorily high fungicidal activity against a wide variety of the fungal pests infesting the crop plants. A further object of this invention is to provide a new 1,2,4-triazole derivative which is of a low toxicity and usable with safety and is useful as a broad-spectrum fungicide. Another objects of this invention will be clear from the following descriptions.

We, the present inventors, have synthetized a number of new 1,2,4-triazole derivatives, and we have now found that a particular class of the new 1,2,4-triazole derivatives now synthetized which is represented by the general formula [I] shown hereinafter has a satisfactorily high fungicidal activity against a wide variety of fungi and exhibits a high preventive effect as well as a high curative effect for treatment of the fungal infections of crop plants. Besides, the new 1,2,4-triazole derivative of the general formula [I] has neither any objectionable phytotoxicity to crop plants, nor any objectionable toxicity to mammalian animals and fishes. It has been found that the new 1,2,4-triazole derivative of the general formula [I] and a salt thereof with an acceptable, inorganic or organic acid, as well as a complex salt thereof with a metal salt have very excellent properties as fungicidal agent of agricultural and horticultural utilities.

According to a first aspect of this invention, therefore, there is provided as the new compound a 1,2,4-triazole derivative of the general formula

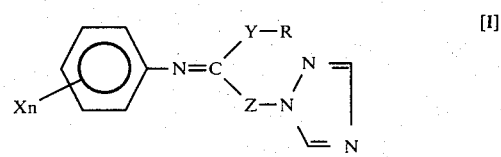

wherein X may be the same or different and denotes a halogen atom, a $(C_1-C_4)$alkyl group, a $(C_1-C_4)$alkoxyl group, a $(C_1-C_4)$alkylthio group, a $(C_1-C_4)$alkylsulfinyl group, a $(C_1-C_4)$alkylsulfonyl group, a trifluoromethyl group, a nitro group or a cyano group;

n is an integer of 0 to 5;

R denotes a $(C_1-C_4)$alkyl group, a $(C_2-C_4)$alkenyl group, a $(C_2-C_4)$alkynyl group, a $(C_1-C_4)$alkoxy-$(C_1-C_4)$alkyl group, a $(C_1-C_4)$alkylthio-$(C_1-C_4)$alkyl group, a $(C_3-C_6)$cycloalkyl group, a $(C_3-C_6)$cycloalkyl-$(C_1-C_4)$alkyl group, a phenyl group, a mono-halophenyl group, a di-halophenyl group, a tri-halophenyl group, or a phenyl$(C_1-C_4)$alkyl group of which the phenyl may optionally bear up to three substituents selected from a halogen atom, a $(C_1-C_4)$alkyl group, a $(C_1-C_4)$alkoxyl group, a $(C_1-C_4)$alkylthio group, a $(C_1-C_4)$alkylsulfonyl group, trifluoromethyl group, cyano group and nitro group, these substituents being the same or different from each other;

Y denotes an oxygen atom or a sulfur atom; and

Z denotes a linear or branched $(C_1-C_6)$alkylene group, or a salt of said 1,2,4-triazole derivative.

The 1,2,4-triazole compound of the general formula [I] may be termed as an O-ether of 1-(1,2,4-triazole-1-yl)-isoalkanoic acid anilide or an S-ether of 1-(1,2,4-triazole-1-yl)-isothioalkanoic acid anilide or a derivative thereof and may also be termed as an N-substituted 1,2,4-triazole-1-yl-alkylamino acid ester or an N-substituted 1,2,4-triazole-1-yl-alkylthioimino acid ester or a derivative thereof.

According to a first embodiment of the first aspect invention, there is provided as the new compound a 1,2,4-triazole derivative which is of the formula

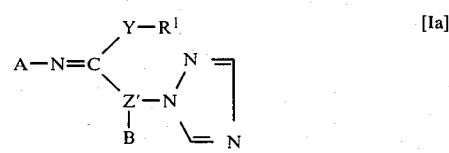

wherein A denotes a phenyl group, a chlorophenyl group, a bromophenyl group, a fluorophenyl group, an iodophenyl group, a cyanophenyl group, a nitrophenyl group, a trifluoromethylphenyl group, a dichlorophenyl group, a dibromophenyl group, a difluorophenyl group, a bromochlorophenyl group, a chlorofluorophenyl group, a chloroiodophenyl group, a trifluoromethylchlorophenyl group, a trichlorophenyl group, a dichlorofluorophenyl group, a methylchlorophenyl group, a methylnitrophenyl group, a methylcyanophenyl group, a trifluoromethyl-methylphenyl group, a trifluoromethyl-dichlorophenyl group, a methoxychlorophenyl group, a methoxydichlorophenyl group, a ($C_1$–$C_4$)alkylphenyl group, a di-($C_1$–$C_4$)alkylphenyl group, a ($C_1$–$C_4$)alkoxyphenyl group, a ($C_1$–$C_4$)alkylthiophenyl group, a ($C_1$–$C_4$)alkylsulfinylphenyl group, a ($C_1$–$C_4$)alkylsulfonylphenyl group or a ($C_1$–$C_4$)alkylsulfonyl-bromophenyl group;

$R^1$ denotes a ($C_1$–$C_4$)alkyl group, a ($C_2$–$C_4$)alkenyl group, a ($C_1$–$C_4$)alkoxy-($C_1$–$C_4$)alkyl group, a methylthio-($C_1$–$C_4$)alkyl group, a cyclohexyl group, a cyclopentyl group, a cyclopentyl-($C_1$–$C_4$)alkyl group, a benzyl group, a chlorobenzyl group, a fluorobenzyl group, an iodobenzyl group, a cyanobenzyl group, a nitrobenzyl group, a dichlorobenzyl group, a trichlorobenzyl group, a chlorobromobenzyl group, a chlorofluorobenzyl group, a chlorocyanobenzyl group, a chloro-trifluoromethylbenzyl group, a mono- or di-($C_1$–$C_4$)alkylbenzyl group, a ($C_1$–$C_4$)alkoxybenzyl group, a ($C_1$–$C_4$)alkyl-chlorobenzyl group, a ($C_1$–$C_4$)alkylnitrobenzyl group, a ($C_1$–$C_4$)alkylthiobenzyl group, a methylsulfonylbenzyl group, a methylsulfonyl-chlorobenzyl group, an ethylsulfinylbenzyl group, a phenylethyl group, a methyldichlorophenylethyl group, a 1-phenyl-propyl group, a 1-chlorophenyl-propyl group, a 1-phenyl-ethyl group, a phenyl group, a chlorophenyl group, a dichlorophenyl group, a dichlorofluorophenyl group, or a ($C_2$–$C_4$)alkynyl group;

Y is an oxygen atom or a sulfur atom;

Z' is a linear ($C_1$–$C_3$)alkylene group; and

B is a hydrogen atom or a ($C_1$–$C_4$)alkyl group, or a salt of said 1,2,4-triazole derivative.

With the 1,2,4-triazole compound of the formula [Ia], it is preferred that A is a chlorophenyl group, a fluorophenyl group, a trifluoromethylphenyl group, a dichlorophenyl group, a chlorofluorophenyl group or a trifluoromethyl-chlorophenyl group, that $R^1$ is a benzyl group, a monochlorobenzyl group or a dichlorobenzyl group; that Z' is a methylene group (—$CH_2$—) when B is the hydrogen atom; and that Z' is a methine group (>CH—) when B is the methyl group.

The 1,2,4-triazole compound of the formula [Ia] is most preferably such ones where Y is the sulfur atom; A is a chlorophenyl group, a fluorophenyl group, a trifluoromethylphenyl group, a dichlorophenyl group, a chlorofluorophenyl group or a trifluoromethyl-chlorophenyl group; $R^1$ is a benzyl group, a monochlorobenzyl group or a dichlorobenzyl group; Z' is a methylene group when B is the hydrogen atom, or Z' is a methine group when B is the methyl group.

According to a second embodiment of the first aspect invention, there is provided as the new compound 1,2,4-triazole derivative which is of the formula

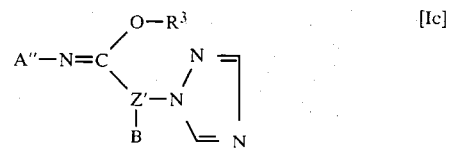

wherein A' denotes a 2,4-dichlorophenyl group, a 2-chloro-4-fluorophenyl group, or a 2-trifluoromethyl-4-chlorophenyl group;

$R^2$ denotes a benzyl group, a 4-chlorobenzyl group, a 2,4-dichlorobenzyl group or a 3,4-dichlorobenzyl group, and B' denotes a hydrogen atom or a methyl group, or a salt of said 1,2,4-triazole derivative.

According to a third embodiment of the first aspect of this invention, there is provided as the new compound a 1,2,4-triazole derivative which is of the formula

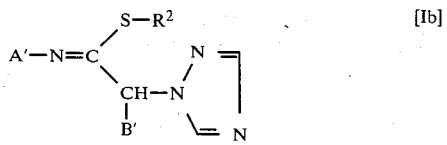

wherein A" denotes a phenyl group, a chlorophenyl group, a bromophenyl group, a fluorophenyl group, an iodophenyl group, a cyanophenyl group, a nitrophenyl group, a trifluoromethyl group, a dichlorophenyl group, a difluorophenyl group, a bromochlorophenyl group, a chlorofluorophenyl group, a chloroiodophenyl group, a trifluoromethylchlorophenyl group, a trichlorophenyl group, a dichlorofluorophenyl group, a methylchlorophenyl group, a methylnitrophenyl group, a methylcyanophenyl group, a trifluoromethyl-dichlorophenyl group, a methoxychlorophenyl group, a methoxy-dichlorophenyl group, a ($C_1$–$C_4$)alkylphenyl group, a di-($C_1$–$C_4$)alkylphenyl group, a ($C_1$–$C_4$)alkoxyphenyl group, a ($C_1$–$C_4$)alkylthiophenyl group, a ($C_1$–$C_4$)alkylsulfonylphenyl group or a ($C_1$–$C_4$)alkylsulfonyl-bromophenyl group;

$R^3$ denotes a ($C_1$–$C_4$)alkyl group, a ($C_2$–$C_4$)alkenyl group, a ($C_1$–$C_4$)alkoxy-($C_1$–$C_4$)alkyl group, a methylthio-($C_1$–$C_4$)alkyl group, a cyclohexyl group, a cyclopentyl group, a cyclopentyl-($C_1$–$C_4$)alkyl group, a benzyl group, a chlorobenzyl group, a fluorobenzyl group, a cyanobenzyl group, a dichlorobenzyl group, a chlorobromobenzyl group, a chlorofluorobenzyl group, a chlorocyanobenzyl group, a mono- or di-($C_1$–$C_4$)alkylbenzyl group, a ($C_1$–$C_4$)alkoxybenzyl group, a ($C_1$–$C_4$)alkyl-chlorobenzyl group, a ($C_1$–$C_4$)alkyl-nitrobenzyl group, a ($C_1$–$C_4$)alkylthiobenzyl group, a methylsulfonylbenzyl group, a phenylethyl group, a methyldichlorophenylethyl group, a 1-chlorophenyl-propyl group, a 1-phenyl-ethyl group, a phenyl group, a chlorophenyl group, a dichlorophenyl group, a dichlorofluorophenyl group, or a ($C_2$–$C_4$)alkynyl group;

Z' is a linear ($C_1$–$C_3$)alkylene group; and

B is a hydrogen atom or a ($C_1$–$C_4$)alkyl group, or a salt of said 1,2,4-triazole derivative.

Although any particular reference is not made in the specification, it may add that the compound of the formula [I] contains the double-bonded linkage —C=N— in the molecule thereof and hence may include geometric isomers thereof and sometime include geometric isomers and/or optical isomers thereof, depending on the nature of the groups R and Z shown in the formula. The new compound of this invention includes all isomers thereof, either isolated or in mixture at any ratio of the respective isomers.

Particular examples of the new 1,2,4-triazole compounds of this invention are listed in Table 1 given hereinafter.

Referring to Table 1, the most preferred compounds of this invention include: Compound Nos. 123, 129, 131, 142, 204, 210, 214, 279, 280, 284, 292 and 293.

The new 1,2,4-triazole compound of the formula [I] according to this invention belongs to a derivative of isoamides or isothioamides and is not described in any chemical literatures. The new 1,2,4-triazole compound of this invention is superior to the previously known fungicidal 1,2,4-triazole compounds in respect of the fungicidal activity to fungi of the fungal infections of crop plants. Thus, the new compound of this invention exhibits a wide ranged antifungal spectrum and is effective for treatment of a wide variety of fungal diseases of plants. In particular, the compound of this invention is effective to control fungal diseases of cereals such as leaf rust (*Puccinia recondita*), stripe rust (*Puccinia striformus*), stem rust (*Puccinia graminis*) or dwarf leaf rust (*Puccinia hordei*) in wheat or barley; powdery mildew (*Erysiphe graminis*) in wheat and barley, leaf spot (*Helminthosporium maydis*) in rice, brown spot (*Cochliobolus setariae*) in corn; fungal diseases of beans such as rust (*Phakopsora pachyrhizi*) in soybean; rust (*Uromyces fabae*) in broad bean, and anthracnose (*Collectotrichum lindemthianum*) in kidney-bean; as well as fungal diseases of vegetables such as powdery mildew (*Sphaerotheca fuliginea*) in cucumber. Fusarium wilt (Fusarium oxysporum f. sp. *cucumerinum*) in cucumber, gummy stem blight (*Mycoshaerella melonis*) in cucumber, powdery mildew (*Sphaerotheca fuliginea*) in water melon, powdery mildew (*Erysiphe cichoracearum*) in egg plant and powdery mildew (*Leveillula taurica*) in sweet pepper; fungal diseases of cucurbitaceae such as anthracnose (*Colletotrichum lagenarium*) in cucumber, anthracnose (*Colletotrichum lagenarium*) in water melon, and anthracnose in sweet melon, and rust (*Puccinia allii*) in onion or stone-leek. The new compound of this invention is also effective even at a low rate of application to control fungal diseases of fruit-plants such as rust (*Gymnosporangium yamadae*), scaf (*Venturia inaequalis*) in apple, powdery mildew (*Podosphaera leucotricha*) in apple, rust (*Gymnosporangium haraeanum*), scab (*Venturia mashicola*) in pear, or rip rot (*Glomerella cingulata*) in grape. When the compound of this invention is used as seed disinfectant, it is highly effective to prevent brown spot and bakanae disease (*Gibberella fujikuroi*) on rice, and smuts (*Urocystis tritici* or *Ustilago hordei*) on barley and wheat, and barely bunt (*Tilletia pancicii*) on barley or wheat bunt (*Tilletia canie*) on wheat, and others.

The compound of this invention is much more effective for preventative treatment of the fungal diseases of plants and also much more effective for curative (protective) of the fungal diseases, as compared to the previously known fungicidal 1,2,4-triazole compounds. Amongst the fungicidal compounds which have been used as the antifungal agent for treatment of fungal diseases of plants in practice, only a few of them is known to exert the curative effects to a satisfactory extent in fields, and much less fewer compounds are known to exert highly favorable results both in the preservative treatment and in the curative treatment of the fungal diseases of plants. Although the compound of this invention shows a high fungicidal activity, it has not or little phyto-toxicity to the useful plants and has not any objectionable toxicity to men and animals and also to fishes. Accordingly, the compound of this invention can be utilized with safety. Thus, the compound of this invention is highly safe as the fungicidal agent of agricultural and horticultural utilities and besides it is highly effect not only in the preventative treatment but also in the curative treatment of the various, fungal diseases of plants, so that the compound of this invention is greatly promising in the fields of agriculture and horticulture.

The 1,2,4-triazole compound of the formula [I] according to this invention can be produced, for example, by three different processes which are shown by the reaction equations (a), (b) and (c) given below, respectively.

In accordance with the first process, the 1,2,4-triazole compound of the formula [I] is produced by reacting an N-substituted α-(1,2,4-triazole-1-yl)alkyl-imino (or thioimino)-acid halide or a reactive equivalent thereof having the formula [II] given below, with an alcohol or a mercaptan having the formula [III] given below, according to the following reaction equation (a):

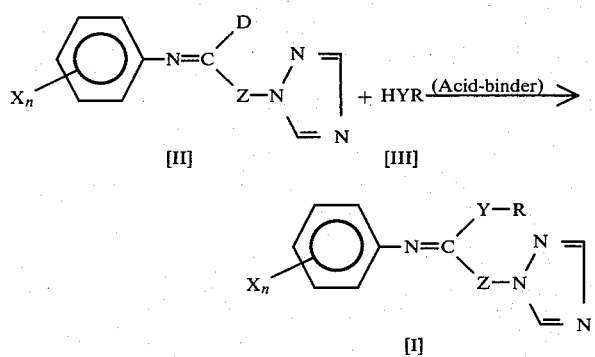

wherein X, n and Z appearing in the formula [II] have the same meanings as defined in the formula [I] and D is a halogen atom such as chlorine or bromine, imidazol-1-yl group, 1,2,4-triazol-1-yl, an alkylsulfonyl group such as mesyl or an aryl-sulfonyl group such as tosyl group and wherein Y and R in the formula [III] have the same meanings as defined in the formula [I].

The starting compound of the general formula [II] is containing the 1,2,4-triazole group like to the 1,2,4-triazole compound of the general formula [I] and hence may be provided also in the form of a salt thereof with an inorganic acid or organic acid or in the form of a metal salt complex. The reactant compound of the general formula [III] contains the groups Y and R which are the same as those present in the final product compound of the formula [I], respectively. The reactant compound [III] belongs to the class of alcohols or mercaptans and may readily be prepared by known chemical methods.

In carrying out the reaction of the compound [II] with the compound [III] according to the reaction equation (a), any solvent serving as the reaction medium may not always be used, though usually an organic solvent may preferably be used. In some cases, an excess of the compound [III] may be used as the solvent. The organic solvent suitable for this purpose includes hydrocarbons, halogenated hydrocarbons, ethers, ketones, nitriles, acid-amides, dimethylsulfoxide and the like. If necessary, it is possible to provide the presence of an amount of an acid-binder which will bind the hydrogen halide as liberated during the reaction. However, the use of the acid-binder is not always required, as both the compound [II] and the compound [I] themselves are basic compounds. The acid-binder as used may be an organic amine such as triethylamine and pyridine or may be an inorganic base such as potassium carbonate and the like. The compound of the formula [III] may be provided in the form of its sodium or potassium salt (alcoholate or mercaptide) which has previously been prepared by reacting it with metallic sodium, metallic potassium, sodium amide or sodium hydride. The reaction may proceed at ambient temperature but may be promoted at an elevated temperature to be completed in a shorter reaction time. When the acid-binder is used, the reaction solution may be filtered after completion of the reaction, so that the salt of the acid-binder deposited in the reaction solution is removed. The resultant filtrate is distilled to remove the solvent for recovery of the compound of the invention. Alternatively, the reaction solution may be admixed with a volume of a water-immiscible organic solvent such as benzene, chloroform, ethylether or tetrahydrofuran and also with a volume of water and the admixture obtained is stirred, followed by separation of the organic phase from the aqueous phase and by removal of the organic solvent from the organic phase by distillation to afford the compound of the invention. The first process as above for producing the compound of this invention according to the reaction equation (a) is illustrated with reference to Examples 1~4 given later.

In accordance with the second process, the 1,2,4-triazole compound of the formula [I] may be produced by reacting an N-substituted imino-ether or thioiminoether of the formula [IV] given below, with 1,2,4-triazole of the formula [V] according to the following reaction equation (b):

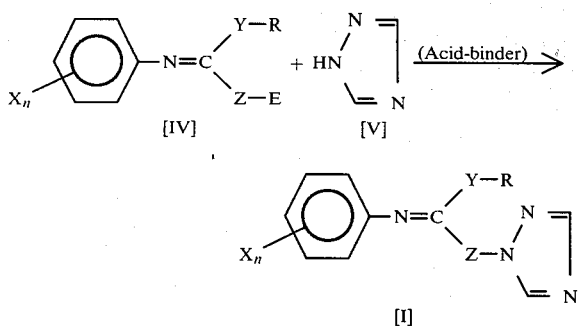

wherein X, n, R and Y appearing in the formula [IV] are as defined hereinabove and E is a halogen atom such as chlorine or bromine, an alkylsulfonyl group such as mesyl or an arylsulfonyl group such as tosyl or benzenesulfonyl. The compound of the formula [V], namely 1,2,4-triazole is morphoteric and may be provided either as a salt of the anion-form of 1,2,4-triazole with an alkali metal cation, or as a salt of the cation-form of 1,2,4-triazole with an inorganic or organic acid or as a salt complex of the cation-form of 1,2,4-triazole with a metal salt.

In carrying out the reaction of the compound [IV] with the compound [V] according to the reaction equation (b), any solvent serving as the reaction medium is not necessary to be used, but usually an organic solvent may preferably be used as the reaction medium. In some cases, an excess of the compound of the formula [V] may be present as the reaction medium solvent. The organic solvent available for this purpose includes hydrocarbons, halogenated hydrocarbons, ethers, esters, ketones, nitriles, alcohols, acid amides, dimethylsulfoxide and the like. The presence of a polar organic solvent is useful to reduce the required reaction time. As the compound [V] is basic, it is not necessary to provide the presence of an additional acid-binder in the reaction mixture. If desired, however, it is possible to use an organic amide such as triethylamine and pyridine or an inorganic base such as potassium carbonate as the acid-binder. The compound of the formula [V] may be provided in the form of its salt which has previously been prepared by reacting it with metallic sodium, metallic potassium, sodium amide or sodium hydride. The reaction may proceed at ambient temperature but a required reaction time may be reduced by warming the reaction mixture.

When the acid-binder is used in the reaction (b), the reaction solution is filtered after completion of the reaction to remove the salt of the acid-binder as formed during the reaction. The filtrate is distilled to remove the organic solvent and the compound of this invention is recovered. Alternatively, the reaction solution may be admixed with a volume or a water-immiscible organic solvent such as benzene, chloroform, ethylether or tetrahydrofuran and also with a volume of water, and the whole admixture is stirred, followed by separation of the organic phase from the aqueous phase and further by removal of the organic solvent from the organic phase by distillation to afford the compound of the invention.

The second process as above for producing the compound of the invention according to the reaction equation (b) is illustrated by Examples 5 and 6 given later.

In accordance with the third process, the compound of the invention may be made by reacting an N-substituted amide compound of the formula [VI] given below, with a halide compound or a reactive equivalent thereof having the formula [VII] given below, according to the following reaction equation (c):

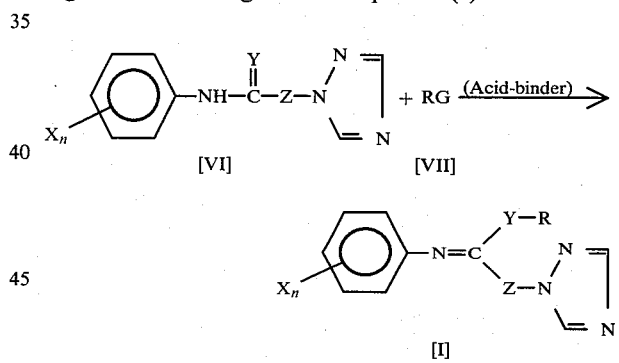

wherein X, n, Y and Z appearing in the general formula [VI] are as defined hereinbefore. The starting compound of the formula [VI] contains the 1,2,4-triazolyl group and may be provided in the form of a salt with an inorganic or organic acid or in the form of a metal salt complex. In the reactant compound of the general formula [VIII], the group R has the same meaning as that present in the compound of the general formula [I], and the group G denotes a halogen atom such as chlorine or bromine, an alkylsulfonyl group such as mesyl or an arylsulfonyl group such as tosyl. The reactant compound [VII] may easily be prepared by known chemical processes.

The process of producing the compound [I] according to the reaction equation (c) may be carried out with advantage, particularly when the starting compound [VI] contains a sulfur atom as a value of Y. The reaction of the compound [VI] with the compound [VII] according to the reaction equation (c) may be conducted without any solvent as the reaction medium. Usually, however, an organic solvent may preferably be provided as the reaction medium. If desired, an excess of the compound [VII] may be utilized as the reaction medium solvent. The organic solvent available for this purpose includes hydrocarbons, halogenated hydrocarbons, ethers, esters, ketones, nitriles, alcohols, dimethylsulfoxide and the like. As the compound [VI] is basic, it is not necessary to provide the presence of an additional acid-binder in the reaction mixture. If desired, however, it is preferable to use an organic amine such as triethylamine and pyridine or an inorganic base such as potassium carbonate as the acid-binder. The compound of the formula [VI] may be provided in the form of its salt which has previously been prepared by reacting it with metallic sodium, metallic potassium, sodium amide or sodium hydride or an alkali metal alcoholate. The reaction may proceed at ambient temperature but a required reaction time may be reduced by warming the reaction mixture. When the acid-binder is used in the reaction (c), the reaction solution is filtered after completion of the reaction to remove the salt of the acid-binder as deposited during the reaction. The filtrate is distilled to remove the organic solvent and the compound of this invention is recovered. Alternatively, the reaction solution may be admixed with a volume of a water-immiscible organic solvent such as benzene, chloroform, ethylether or tetrahydrofuran and also with a volume of water, and the whole admixture is stirred, followed by separation of the organic phase from the aqueous phase and further by removal of the organic solvent from the organic phase by distillation to afford the compound of the invention.

The third process as above for producing the compound of the invention according to the reaction equation (c) is demonstrated by Example 7 shown later.

The 1,2,4-triazole compound of the formula [I] according to the invention may be in the form of its salt which includes a salt of the 1,2,4-triazole compound with an inorganic acid or a salt of the 1,2,4-triazole compound with an organic acid and a salt complex of the 1,2,4-triazole compound with a metal salt.

The inorganic acid suitable for the salt formation includes: hydrohalogenic acids such as hydrochloric, hydrobromic or hydroiodic acid; sulfuric acid, nitric acid, perchloric acid, phosphoric acid and sulfamic acid. The preparation of the salt of the 1,2,4-triazole compound with an inorganic acid may be achieved by dissolving or suspending the 1,2,4-triazole compound [I] in water or a suitable organic solvent and admixing the resultant solution or suspension with a stoichiometrical quantity of the acid which may be provided as such or may have been diluted with the organic solvent. If the acid used is gaseous, it may be blown into the solution or suspension of the 1,2,4-triazole compound. Generally, this salt-forming reaction may proceed rapidly at ambient temperature or even under cooling. When the inorganic acid salt formed is deposited as crystals, these may be separated by filtration. In some cases, the salt-forming reaction solution may be distilled to remove the solvent therefrom, affording the compound of this invention in the salt form. The preparation of the inorganic acid salt of the compound of this invention is illustrated by Examples 8~9.

The organic acid suitable for the salt formation includes: a saturated or unsaturated aliphatic acid, either substituted or unsubstituted; an arylcarboxylic acid such as benzoic acid; an alkyl- or aryl-sulfonic acid; a mono- or di-substituted alkyl- or aryl-sulfonic acid; and esters and amides of phosphoric acid or phosphonic acid, including their sulfur homologues. Particular examples of the suitable acids for this purpose may be, for example, dichloroacetic acid, trichloroacetic acid, oxalic acid, maleic acid, 2,4,6-trinitrobenzoic acid, methanesulfonic acid, octylsulfonic acid, benzenesulfonic acid, toluenesulfonic acid, dimethylsulfamic acid, cyclohexylsulfamic acid, phenylsulfamic acid, O,O-diethylphosphoric acid, O,O-diethylmonothiophosphoric acid, O,O-diethyldithiophosphoric acid, O-ethyl-phenylphosphonic acid, O-ethylphosphoric acid or phenylphosphonic acid. The formation of the salt of the 1,2,4-triazole compound with an organic acid may be achieved by dissolving or suspending the compound [I] in water or a suitable organic solvent and admixing the resultant solution or suspension with a stoichiometric quantity of the organic acid which may optionally have been diluted with water or with the organic solvent. The salt-forming reaction may proceed at ambient temperature or even under cooling. The reaction mixture may be heated, if necessary. When the organic acid salt of the 1,2,4-triazole compound as formed is deposited as crystals, these may be separated by filtration. In some cases, the compound of the invention in the salt form may be recovered by removing the solvent from the salt-forming reaction solution by distillation. The preparation of the organic acid salt of the 1,2,4-triazole compound of the invention is illustrated by Examples 10~11.

The cation present in the metal salt suitable for formation of the complex salt of the 1,2,4-triazole compound [I] includes: metal cations such as copper, manganese, zinc, cobalt, nickel, iron, aluminum, silver, magnesium, tin, calcium and the like. The anion present in such metal salt includes an inorganic anion such as chlorine, bromine, iodine, fluorine anion; sulfuric, nitric or phosphoric acid anion; as well as an organic anion such as formic, acetic, methanesulfonic or toluenesulfonic acid anion and the like. The formation of the complex salt of the 1,2,4-triazole compound [I] with a metal salt may be achieved usually by reacting the compound [I] with a metal salt in water or an inert organic solvent. The inert organic solvent available for this purpose may be water, methanol, acetonitrile, dioxane, ethyl ether, dichloromethane, chloroform or hexane. The compound [I] and the metal salt reactant may properly be reacted with each other in a stoichiometrical or substantially stoichiometric molar proportion. When some metal cation is used for formation of the complex salt, there are formed two complexes of which the ligands are different from each other. The complex-forming reaction usually can proceed at ambient temperature without the necessity of heating the reaction mixture. If the complex salt of the imidazole compound with the metal salt is deposited as crystals, the latter may be recovered by filtration to afford the compound of the invention in the complex form. In some cases, the complex-forming reaction solution may be distilled to remove the solvent therefrom, yielding the complex form of the compound of the invention. The preparation of the metal salt complex is demonstrated by Examples 12~13 shown later.

The 1,2,4-triazole compound of the invention may be used as such for anti-fungal agent but more conveniently formulated into compositions for such antifungal purposes.

This invention, therefore, provides a fungicidal composition comprising, as an active ingredient, 1,2,4- triazole compound of the general formula [I] or a salt thereof, in association with an acceptable carrier for the active ingredient.

The invention further provides a method of combating the fungal pests of plants, which comprises treating plants, seeds or trees with a 1,2,4-triazole compound of the formula [I] or a salt thereof as hereinbefore described.

The compound of the invention can be used to combat the fungal pests of plants or seeds in a number of ways, and for example, the compound of the invention as such or in the form of a formulation can be applied directly to the foliage of a plant which is infected or likely to become infected, or they can be applied also to bushes and trees, to seeds or to other medium in which plants, bushes or trees are growing or are to be planted, or they can be sprayed on, dusted on or applied as a cream. Application can be made to any part of the plant, bush or tree, for example, to the foliage, stems, branches or roots, or to soil surrounding the roots.

The term "treating" as used means all these ways of application and the term "plant" includes seedlings, bushes and trees.

The compound of the invention are preferably used for agricultural and horticultural purposes in the form of a composition. The type of composition used in any instance will depend upon the particular purpose envisaged.

Generally, the composition of this invention may comprise any of the additive which are conventionally employed in the formulations of agricultural and horticultural usages, such as emulsifying agents, wetting agents, extending agents, dispersion agents and degradation-preventors, by which the effects of the composition as applied can be sured for the intended pesticidal purposes.

The composition of this invention may be prepared by formulating the compound of the general formula [I] into the form of emulsifiable concentrate, wettable powder, sol (flowable powder), dusting powder, driftless (DL-type) powder, small granules or granules etc., according to conventional formulation technique. The carrier material which may be admixed with the active compound of this invention may be any solid or liquid ones which have been used conventionally in the preparations of agricultural and horticultural usages. The liquid carrier available in the formulation of this invention includes various solvents, such as, water, aromatic hydrocarbons, aliphatic hydrocarbons, alcohols, esters, ketones, acid amides, dimethylsulfoxide and the like. The solid carrier includes mineral powders such as clay, talc, kaolin, bentonite, diatomaceous earth, calcium carbonate and silica and the like, as well as organic powders such as wood powder and others.

More particularly, the composition of this invention may be in the form of dusting powder in which the active compound is mixed with a solid carrier such as kaolin, bentonite, or it may be in the form of granules in which the active compound is absorbed in a porous granular material such as pumice.

The composition of this invention may also be in the form of liquid preparations to be used as dips or sprays, which are usually aqueous dispersion or emulsion of the active ingredient compound of this invention together with one or more of the known wetting agents, dispersing agents or emulsifying agents.

Wetting agents, dispersing agents and emulsifying agents may be of the cationic, anionic or non-ionic type.

Suitable agents of the cationic type may be, for example, quaternary ammonium compounds, for example, cetyltrimethyl ammonium bromide. Suitable agents of the anionic type may be, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and the sodium salts of diisopropyl- or triisopropylnaphthalene sulphonates. Suitable agents of the non-ionic type may be, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters of long chain fatty acids and hexitol anhydrides and the condensation products of the said partial esters with ethylene oxide. The composition of the invention may contain a thickening agents such as gum, aliphatic acid salt, methylcellulose and the like.

The compositions to be used as sprays may also be in the form of aerosols wherein the formulation is charged in a container under pressure together with a propellant such as fluorotrichloromethane or dichlorodifluoromethane. The compositions to be used in the form of aqueous dispersions or emulsions are generally supplied in the form of a concentrate containing a high proportion of the active ingredient compound, and said concentrate may be diluted with water before use. These concentrates are often required to withstand storage for prolonged periods and after such storage, to be capable of dilution with water to form aqueous preparations which remain homogeneous for a sufficient time to enable them to be applied by conventional spray equipment.

The composition of this invention in the form of the concentrates such as wettable powder, liquid preparations and emulsifiable concentrate may contain the active compound of the invention in an amount of 1 to 95% by weight and usually of 2 to 75% by weight based on the whole weight of the composition. These preparations may be diluted with water upon use to give an aqueous preparation containing 0.0001 to 10% by weight of the active compound. The powders and granules may contain 0.1 to 10% by weight of the active compound. Such concentrates as oily solution or dispersion, emulsifiable concentrates and sol (flowable powder) may directly be applied as the apraying formulation at a minimized rate of application, without being diluted with water before use. The wettable powder or other powders may be used as such as the seed-dressing agent to overcoat the seeds of crop plants. The seeds may also be dipped in the liquid formulation which is prepared by diluting the wettable powder, sol or emulsifiable concentrate with water.

When the compound of this invention is used as the fungicidal agent of agricultural and horticultural utilities, it may be applied in admixture with insecticides, another fungicides, bactericides, herbicides, plant-growth regulators and others, for broadening the range of applicability that the compound of this invention can be used effectively for the intended pesticidal purposes. In some cases, synergism can be expected by the combined use of the compound of this invention with another pesticides.

Examples of fungicides and bactericides which may be used in admixture with the compounds of this invention include the following:

Carbamate fungicides such as 3,3'-ethylenebis(tetrahydro-4,6-dimethyl-2H-1,3,5-thiadiazine-2-thione), zinc or manganese ethylenebis(dithiocarbamate), bis(dimethyldithiocarbamoyl)disulfide, zinc propylenebis(dithiocarbamate), bis(dimethyldithiocarbamoyl)ethylenediamine; nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6p-diethylphenyl)phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicide such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiadiazole; 2,4-dichloro-6-(O-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-i,j]quinoline-2-one; 3'-isopropoxy-2-methyl-benzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethylaminopropyl)thiocarbamate hydrochloride; piomycin; S,S-6-methylquinoxaline-2,3-diyldithiocarbonate; complex of zinc and manneb; di-zinc bis(dimethyldithiocarbamate)ethylenebis (dithiocarbamate).

Examples of plant growth regulators and herbicides which may be used in combination with the compounds of this invention includes the following: isourea plant growth regulators such as N-methoxycarbonyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-s-triazine and 2-methylthio-4-ethylamino-6-isopropylamino-s-triazine; phenoxy herbicides such as 2,4-dichlorophenoxyacetic acid and methyl, ethyl and butyl esters thereof, 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate, S-ethyl-N-cyclohexyl-N-ethylthiolcarbamate and S-ethyl-hexahydro-1H-azepine-1-carbothioate and S-ethyl-N,N-di-n-propylthiocarbamate; pyridinium herbicides such as 1,1'-dimethyl-4,4'-bispyridinium dichloride; phosphoric herbicides such as N-(phosphonomethyl)glycine; aniline herbicides such as $\alpha,\alpha,\alpha$-trifluoro-2,6-dinitro-N,N-dipropyl-p-toluidine, 4-(methylsulfonyl)-2,6-dinitro-N,N-dipropylaniline and $N^3,N^3$-diethyl-2,4-dinitro-6-trifluoromethyl-1,3-phenylene diamine; acid anilide herbicids such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-dimethyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methylphenoxy)pyridazine.

Examples of insecticides which may be mixed with the compounds of this invention include the following: phosphoric insecticides such as O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-2-[(ethylthio)ethyl]phosphorodithioate, O,O-diethyl S-2-[(ethylthio)ethyl]phosphorodithioate, O,O-dimethyl-1-hydroxy-2,2,2-trichloroethylphophonate, O,O-diethyl-O-(5-phenyl-3-isooxazolyl)phosphorothioate, O,O-dimethyl O-(2,5-dichloro-4-bromophenyl)phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6- chloro-2-oxo-3-benzooxazolinyl)methyl]O,O-diethyl phosphorodithioate, 2-chloro-1-(2,4-dichlorophenyl)vinyl diethylphosphate, O,O-diethyl O-(3-oxo-2-phenyl-2H-pyridazine-6-yl)phosphorothioate, O,O-dimethyl S-(1-methyl-2-ethylsulfinyl)-ethyl phophorothiolate, O,O-dimethyl S-phthalimidomethyl phosphorodithioate, O,O-diethyl S-(N-ethoxycarbonyl-N-methylcarbamoylmethyl)phosphorodithioate, O,O-dimethyl S-[2-methoxy-1,3,4-thiadiazol-5-(4H)-onyl-(4)-methyl]dithiophosphate, 2-methoxy-4H-1,3,2-benzooxaphosphorine 2-sulfide, O,O-diethyl O-(3,5,6-trichloro-2-pyridyl)-phosphorothiate, O-ethyl O-2,4-dichlorophenyl thionobenzene phosphonate, S-[4,6-diamino-s-triazine-2-yl-methyl]O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O-N-(methylsulfinyl) phenyl phosphorothioate, O-ethyl S-propyl O-2,4-dichlorophenyl phosphorodithioate and cis-3-(dimethoxyphosphinoxy)N-methyl-cis-crotone amide; carbamate insecticides such as 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis(carbamoylthio)-2-(N,N-dimethylamino)propane hydrochloride and 2-diethylamino-6-methylpyrimidine-4-yl-dimethylcarbamate; and another insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl) 2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin]oxide, 1-(4-chlorophenyl)-3-(2,6-difluorobenzoyl)urea and S-tricyclohexyltin O,O-diisopropylphosphorodithioate.

The compound of this invention may also be admixed with fertilisers such as nitrogen-containing fertiliser or phosphorous-containing fertiliser. The composition may comprises granules of fertiliser which have been coated with the compound of this invention or in which the compound of this invention has been incorporated.

This invention is now illustrated with reference to the following Examples. Examples 1 to 13 are illustrative of the production of the new compound of this invention. Examples 14 to 19 are illustrative of the formulations containing the compound of this invention. Examples 20 to 29 are illustrative of the tests of estimating the fungicidal activities of the compound of this invention.

EXAMPLE 1

Production of Compound No. 12 (identified in Table 1 given later) of the formula

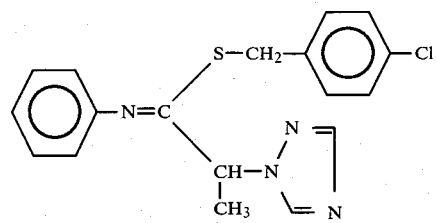

To a mixture of 27.1 g of the compound of the formula

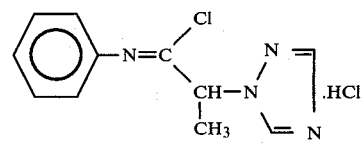

(namely, α-(1,2,4-triazol-1-yl)-propionic acid phenylimidoyl chloride hydrochloride), 16.0 g of p-chlorobenzylmercaptan and 200 ml of acetonitrile was added dropwise 21.0 g of triethylamine (as acid-binder) under ice-cooling. The whole admixture was stirred for 30 minutes at ambient temperature, and the resulting reaction solution was admixed with water and benzene. After stirring the admixture, the organic layer was separated from the aqueous phase and washed with 1N aqueous sodium hydroxide and then with water, followed by drying over anhydrous sodium sulfate. The dried solution was distilled under reduced pressure to remove the solvent, and there was recovered the above titled compound No. 12 (namely, α-(1,2,4-triazol-1-yl)-isothiopropionic acid anilide S-p-chlorobenzyl ether) as a lightly yellow colored oil in a yield of 34.2 g. When this oil was allowed to stand for a while at ambient temperature, it crystallized. Recrystallization of this oil from a mixed solvent of n-hexane and acetone gave a pure product as white-colored crystals of m.p. 71°~72.5° C.

The compound No. 12 may alternatively be named as 4-chlorobenzyl N-phenyl-2-(1,2,4-triazole-1-yl)propanethioimidate.

EXAMPLE 2

Production of Compound No. 106 (identified in Table 1) of the formula

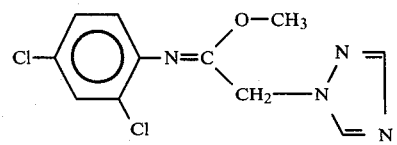

To a mixture of 32.6 g of the compound of the formula

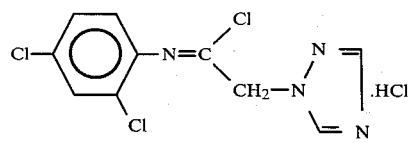

(namely, 1,2,4-triazol-1-yl-acetic acid 2',4'-dichlorophenylimidoyl chloride hydrochloride) and 100 ml of methanol was added dropwise under ice-cooling a solution of sodium methoxide in methanol which was prepared from 4.6 g of sodium metal and 50 ml of methanol. The whole admixture was stirred for 30 minutes at ambient temperature, and the reaction mixture was filtered under suction to remove the salt (sodium chloride) precipitated. The filtrate was concentrated under reduced pressure to afford the above titled compound No. 106 (namely, 1,2,4-triazol-1-yl-isoacetic acid 2',4'-dichloroanilide O-methyl ether) as a lightly yellow colored oil in a yield of 27.6 g. This oil was purified by a silica gel column chromatography to give a pure product as a colorless oil which showed a refractive index $n_D^{23}$ 1.5753.

EXAMPLE 3

Production of compound No. 123 (identified in Table 1) of the formula

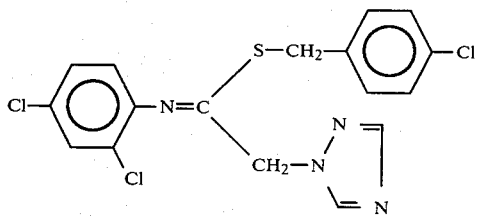

The compound of the formula

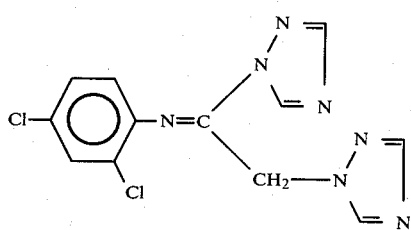

(namely, 1-(1,2,4-triazol-1-yl)-acetic acid 2',4'-dichlorophenylimidoyl)-1,2,4-triazole) (32.2 g) and p-chlorobenzyl mercaptan (16.0 g) were dissolved in a volume of methylisobutylketone, and the resultant solution was refluxed for 5 hours. After cooling, the reaction solution was admixed with water and benzene. The organic layer was separated from the aqueous phase and washed with 1N aqueous sodium hydroxide and then with water, followed by drying over anhydrous sodium sulfate. The dried organic solution was distilled under reduced pressure to remove the solvent, and there was afforded the above titled compound No. 123 (namely, 1,2,4-triazol-1-yl-isothioacetic acid 2',4'-dichloroanilide S-p-chlorobenzyl ether) as faintly yellow colored crystals in a yield of 40.3 g. Recrystallization of this product from a mixed solvent of n-hexane and acetone gave colorless crystals of m.p. 88°~90° C.

EXAMPLE 4

Production of Compound No. 280 (identified in Table 1) of the formula

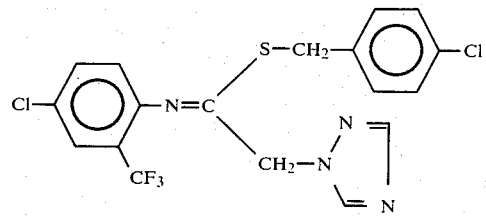

The compound of the formula

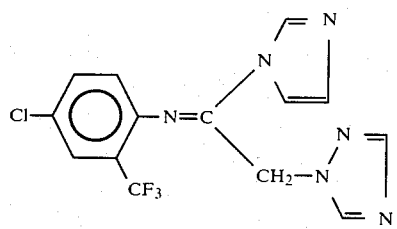

(namely, 1-(1,2,4-triazol-1-yl-acetic acid 4'-chloro-2'-trifluoromethylphenylimidoyl)imidazole) (35.5 g) and p-chlorobenzyl mercaptan (16.0 g) were dissolved in 150 ml of acetonitrile, and the resulting solution was refluxed for 1 hour. After cooling, the reaction solution was admixed with water and benzene. The organic layer was separated from the aqueous phase and washed with 1N aqueous sodium hydroxide and then with water, followed by drying over anhydrous sodium sulfate. The dried organic solution was distilled under reduced pressure to remove the solvent. The above titled compound No. 280 (namely, 1,2,4-triazol-1-yl-isothioacetic acid 4'-chloro-2'-trifluoromethylanilide S-p-chlorobenzyl ether) was afforded as a faintly yellow colored oil in a yield of 43.6 g. This oil was purified by a silica gel column chromatography to give a pure product as a colorless crystals which showed a m.p. 45.5°~48° C.

EXAMPLE 5

Production of Compound No. 80 (identified in Table 1) of the formula

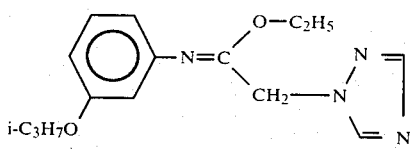

1,2,4-Triazole (6.9 g) was added to a solution of sodium ethoxide in ethanol which had been prepared from 2.3 g of sodium metal and 200 ml of ethanol, and the resultant mixture was refluxed for 2 hours. The reaction solution was cooled and then admixed with 25.6 g of the compound of the formula

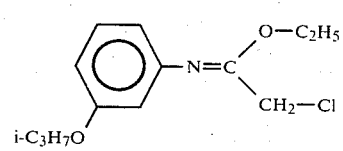

(namely, chloro-isoacetic acid 3-isopropoxyanilide O-ethylether), followed by refluxing for 2 hours. After cooling, the reaction solution obtained was filtered under suction to remove off the salt (sodium chloride) precipitated. The filtrate was concentrated under reduced pressure to give the above titled compound No. 80 (namely, 1,2,4-triazol-1-yl-isothioacetic acid 3'-isopropoxyanilide O-ethylether) as a faintly yellow colored oil in a yield of 26.2 g. This oil was purified by a silica gel column chromatography to give a pure product as a colorless oil which showed a refractive index $n_D^{23}$ 1.6081.

EXAMPLE 6

Production of Compound No. 250 (identified in Table 1)

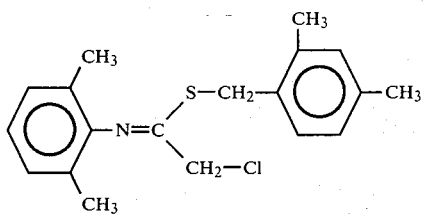

The compound of the formula

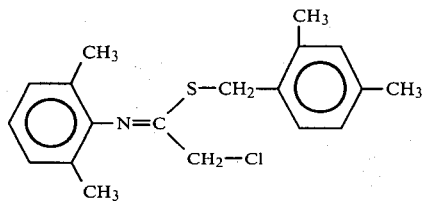

(namely, chloro-isothioacetic acid 2,6-dimethylanilide S-2',4'-dimethylbenzylether) (33.2 g) and 1,2,4-triazole (7.2 g) were dissolved in 100 ml of dimethylformamide, and the resultant solution was heated at 100° C. for 2 hours to effect the reaction. After cooling, the reaction solution was admixed with water and benzene. The organic layer as formed was separated from the aqueous phase and washed with 1N aqueous sodium hydroxide and then with water, followed by drying over anhydrous sodium sulfate. The dried organic solution was distilled under reduced pressure to remove the solvent, and the above titled compound No. 250 (namely, 1,2,4-triazol-1-yl-isothioacetic acid 2',6'-dimethylanilide S-2'',4''-dimethylbenzyl ether) was afforded as faintly yellow colored crystals in a yield of 32.8 g. Recrystallization of this product from a mixed solvent of cyclohexane and acetone gave a pure product as white colored crystals of m.p. 103°~104° C.

EXAMPLE 7

Production of Compound No. 228 (identified in Table 1) of the formula

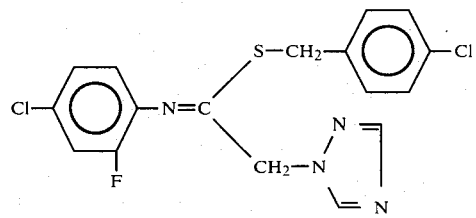

The compound of the formula

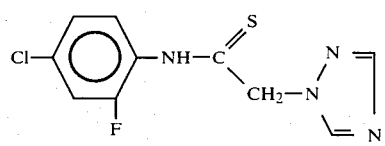

(namely, 1,2,4-triazol-1-yl-thioacetic acid 4'-chloro-2'-fluoroanilide) (23.9 g) was admixed with a solution of sodium ethoxide in ethanol which had been prepared from 2.3 g of sodium metal and 100 ml of ethanol. To the resultant admixture was added a solution of 16.1 g of p-chlorobenzyl chloride in 30 ml of ethanol, and the whole mixture was refluxed for 1 hour. After cooling, the reaction solution was filtered under suction to remove the salt (sodium chloride), and the filtrate was concentrated under reduced pressure, affording 33.4 g of the above titled compound No. 228 (namely, 1,2,4-triazol-1-yl-isothioacetic acid 4'-chloro-2'-fluoroanilide S-p-chlorobenzylether) as faintly yellow colored crystals. Recrystallization of this product from a mixed solvent of cyclohexane and acetone gave a pure product as white colored crystals of m.p. 102°~103.5° C. This product may alternatively be named as 4-chlorobenzyl N-(4-chloro-2-fluorophenyl)-2-(1,2,4-triazol-1-yl)ethanethioimidate.

EXAMPLE 8

Production of Compound No. 5 (identified in Table 1 and in the form of an inorganic acid salt) of the formula

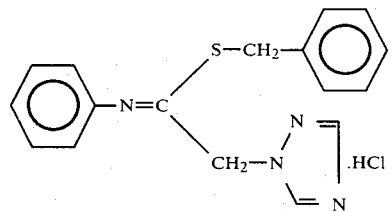

Compound No. 4 of the formula

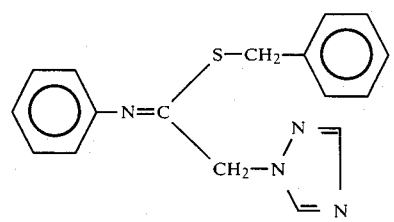

(namely, 1,2,4-triazol-1-yl-isothioacetic acid anilide S-benzylether) (3.1 g) was dissolved in 50 ml of acetone, and the resultant solution was admixed with a solution of 2 ml of 5N aqueous hydrochloric acid in 10 ml of acetone. The admixture obtained was allowed to stand for 1 hour at ambient temperature, followed by removing the deposited crystals by filtration. The crystals so recovered was washed with acetone, affording 3.0 g of the above titled compound No. 5 (namely, 1,2,4-triazol-1-yl-isothioacetic acid anilide S-benzylether hydrochloride) as white colored crystals showing m.p. 77°~79.5° C.

EXAMPLE 9

Production of Compound No. 77 (identified in Table 1 and in the form of an inorganic acid salt) of the formula

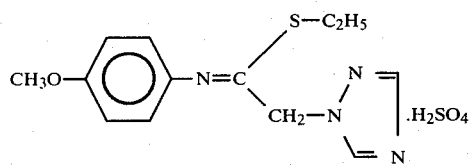

Compound No. 76 of the formula

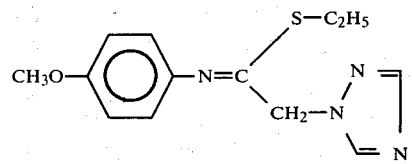

(namely, 1,2,4-triazol-1-yl-isothioacetic acid 4'-methoxyanilide S-ethylether) (2.8 g) was dissolved in 100 ml of acetone, to which was then added 50 ml of n-hexane, followed by stirring the resultant solution for 10 minutes at ambient temperature. The crystals deposited were removed by filtration and washed with a mixed solvent of n-hexane and acetone, yielding 2.9 g of the above titled compound No. 77 (namely, 1,2,4-triazol-1-yl-isothioacetic acid 4'-methoxyanilide S-ethylether sulfate) as faintly yellow colored crystals showing m.p. 106°~109° C.

EXAMPLE 10

Production of Compound No. 112 (identified in Table 1 and in the form of an organic acid salt) of the formula

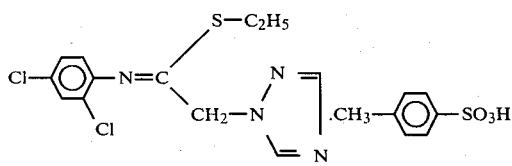

Compound No. 111 of the formula

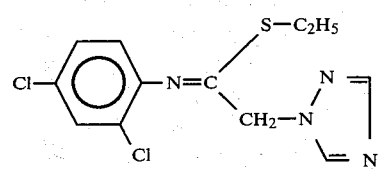

(namely, 1,2,4-triazol-1-yl-isothioacetic acid 2',4'-dichloroanilide S-benzylether) (3.2 g) was dissolved in 100 ml of acetone, to which was then added a solution of 2.0 g of p-toluenesulfonic acid monohydrate in 30 ml of acetone. The mixture obtained was allowed to stand for 2 hours at ambient temperature, followed by removing the deposited crystals by filtration. The crystals so recovered were washed with acetone, yielding 4.7 g of the above titled compound No. 112 (namely, 1,2,4-triazol-1-yl-isothioacetic acid 2',4'-dichloroanilide S-ethylether p-toluenesulfonate) as white colored crystals showing m.p. 142°~144° C.

EXAMPLE 11

Production of Compound No. 205 (identified in Table 1 and in the form of an organic acid salt) of the formula

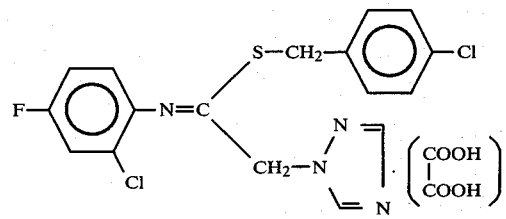

Compound No. 204 of the formula

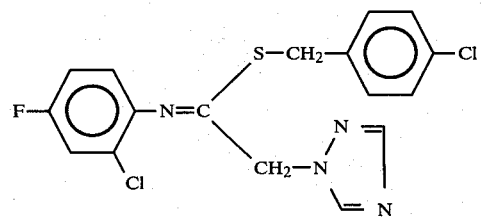

(namely, 1,2,4-triazol-1-yl-isothioacetic acid 2'-chloro-4'-fluoroanilide S-p-chlorobenzylether) (4.0 g) was dissolved in 100 ml of ethylether, to which was then added a solution of 1 g of oxalic acid in 100 ml of ethylether. The mixture was allowed to stand for 2 hours at ambient temperature. The crystals deposited were removed by filtration and washed with ethylether, affording 4.4 g of the above titled compound No. 205 (namely, 1,2,4-triazol-1-yl-isothioacetic acid 2'-chloro-4'-fluoroanilide S-p-chlorobenzylether oxalate) as white colored crystals showing m.p. 143°~145° C.

EXAMPLE 12

Production of Compound No. 39 (identified in Table 1 and in the form of a metal salt complex) of the formula

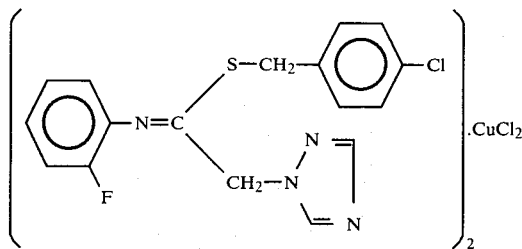

Compound No. 38 of the formula

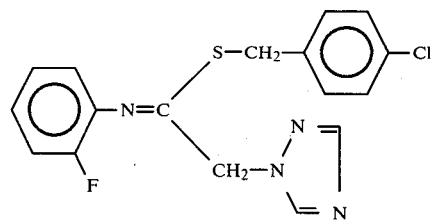

(namely 1,2,4-triazol-1-yl-isothioacetic acid 2'-fluoroanilide S-p-chlorobenzylether) (3.6 g) was dissolved in 100 ml of ethanol, to which was then added 0.8 g of anhydrous cupric chloride. The mixture was allowed to stand for 1 hour at ambient temperature, and the crystals deposited were removed by filtration and washed with ethanol, yielding 3.5 g of the above titled compound No. 39, namely bis-(1,2,4-triazol-1-yl-isothioacetic acid 2'-fluoroanilide S-p-chlorobenzylether) cupric chloride complex as bluish white colored crystals showing m.p. 163°~165° C.

EXAMPLE 13

Production of Compound No. 109 (identified in Table 1 and in the form of a metal salt complex) of the formula Compound No. 108 (3.5 g, the free base form) of Table 1 (namely 1,2,4-triazol-1-yl-isoacetic acid 2',4'-dichloroanilide O-phenylether) was dissolved in 10 ml of methanol, to which was then added 0.7 g of anhydrous nickel chloride. The mixture was stirred for 10 minutes at ambient temperature and the resultant reaction solution was then admixed with 100 ml of n-hexane. The crystals deposited were removed by filtration and washed with n-hexane, yielding 3.4 g of the above titled compound No. 109, namely bis-(1,2,4-triazol-1-yl-isoacetic acid 2',4'-dichloroanilide O-phenylether) nickel chloride complex as bluish white colored crystals showing m.p. 130°~133° C.

Similarly to the procedures of the Examples 1 to 13, further examples of the new compound of the formula [I] were produced. Representative compounds are listed in Table 1 below. In Table 1, the column of "Salts" indicates the nature of the inorganic acid, organic acid or metal salt forming the complex of the compound [I] of the invention, as well as the molar proportion of the compound [I] in the free form which are required to constitute one mole of the complex of the compound of the invention. Compound Numbers shown in Table 1 are referred to in the foregoing and following Examples.

TABLE 1

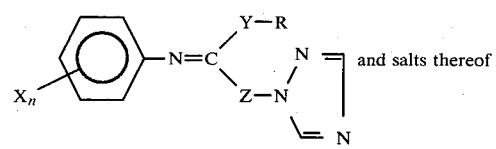

and salts thereof

| Compound No. | $X_n$ | R | Y | Z | Salts Salt-forming component | moles | Refractive index or m.p. (°C.) |
|---|---|---|---|---|---|---|---|
| 1 | H | —CH₃ | O | —CH₂— | | | $n_D^{23}$ 1.6021 |
| 2 | " | —CH₂—⬡—Cl | " | " | | | $n_D^{23}$ 1.6003 |
| 3 | " | —C₂H₅ | S | " | | | $n_D^{23}$ 1.5933 |
| 4 | " | —CH₂—⬡ | " | " | | | $n_D^{23}$ 1.6205 |
| 5 | " | " | " | " | HCl | 1 | m.p. 77~79.5 |
| 6 | " | —CH₂—⬡—Cl | " | " | | | $n_D^{23}$ 1.6306 |

TABLE 1-continued $$\text{X}_n\text{-C}_6\text{H}_4\text{-N=C(Y-R)-Z-N(N=N)-N} \text{ and salts thereof}$$

| Compound No. | $X_n$ | R | Y | Z | Salts Salt-forming component | moles | Refractive index or m.p. (°C.) |
|---|---|---|---|---|---|---|---|
| 7 | " | —CH₂—C₆H₄—F | " | " | | | $n_D^{23}$ 1.6115 |
| 8 | " | —CH₂—C₆H₃Cl₂ (3,4-di-Cl) | " | " | | | m.p. 83.5~85.5 |
| 9 | " | —CH₂—C₆H₃Cl₂ (2,3-di-Cl) | " | " | | | $n_D^{23}$ 1.6330 |
| 10 | " | —C₂H₅ | " | —CH(CH₃)— | | | $n_D^{23}$ 1.5817 |
| 11 | " | —CH₂—C₆H₅ | " | " | | | $n_D^{23}$ 1.6146 |
| 12 | " | —CH₂—C₆H₄—Cl | " | " | | | m.p. 71~72.5 |
| 13 | " | —CH₂—C₆H₄—F | " | " | | | m.p. 97~98 |
| 14 | " | —CH₂—C₆H₃Cl₂ | " | " | | | $n_D^{23}$ 1.6180 |
| 15 | " | —CH₂CH=CH₂ | " | —CH(C₂H₅)— | | | $n_D^{23}$ 1.6166 |
| 16 | " | —CH₂CH₂—C₆H₅ | " | " | | | $n_D^{23}$ 1.6123 |
| 17 | " | —C₆H₃Cl₂ (2,4-di-Cl) | O | —CH(n-C₄H₉)— | | | $n_D^{23}$ 1.6153 |
| 18 | 2-Cl | —n-C₃H₇ | " | —CH₂— | | | $n_D^{23}$ 1.6145 |
| 19 | " | —CH₂—C₆H₅ | S | " | | | $n_D^{23}$ 1.6257 |
| 20 | " | —CH₂—C₆H₄—Cl | " | " | | | $n_D^{23}$ 1.6159 |
| 21 | " | —CH₂—C₆H₄—F | " | " | | | $n_D^{23}$ 1.6108 |
| 22 | " | —CH₂—C₆H₃Cl₂ | " | " | | | m.p. 79.5~82.5 |

TABLE 1-continued

| Compound No. | $X_n$ | R | Y | Z | Salts Salt-forming component | moles | Refractive index or m.p. (°C.) |
|---|---|---|---|---|---|---|---|
| 23 | " | —CH$_2$—(3,4-Cl,Cl-phenyl) | " | " | | | $n_D^{23}$ 1.6367 |
| 24 | " | —CH$_2$—phenyl | O | —CH(CH$_3$)— | | | $n_D^{23}$ 1.6136 |
| 25 | " | " | S | " | | | $n_D^{23}$ 1.6128 |
| 26 | " | —CH$_2$—(4-Cl-phenyl) | " | " | | | $n_D^{23}$ 1.6156 |
| 27 | " | —CH$_2$—(4-F-phenyl) | " | " | | | m.p. 60.5~62 |
| 28 | " | —CH$_2$—(3,4-Cl,Cl-phenyl) | " | " | | | $n_D^{23}$ 1.6203 |
| 29 | 3-Cl | cyclopentyl (H) | O | —CH$_2$— | | | $n_D^{23}$ 1.6201 |
| 30 | " | —C$_2$H$_5$ | S | " | | | $n_D^{23}$ 1.6024 |
| 31 | " | —CH$_2$—phenyl | " | " | | | $n_D^{23}$ 1.6257 |
| 32 | 4-Cl | —C$_2$H$_5$ | " | " | | | $n_D^{23}$ 1.6069 |
| 33 | " | —CH$_2$—phenyl | " | " | | | m.p. 55.5~57.5 |
| 34 | " | —phenyl | O | —CH(n-C$_3$H$_7$)— | | | $n_D^{23}$ 1.6026 |
| 35 | 2-F | —CH$_2$CH$_2$SCH$_3$ | O | —CH$_2$— | | | $n_D^{23}$ 1.6114 |
| 36 | " | —n-C$_3$H$_7$ | S | " | | | $n_D^{23}$ 1.6097 |
| 37 | " | —CH$_2$—phenyl | " | " | | | $n_D^{23}$ 1.6098 |
| 38 | " | —CH$_2$—(4-Cl-phenyl) | " | " | | | m.p. 46~48 |
| 39 | " | " | " | " | CuCl$_2$ | 2 | m.p. 163~165 |
| 40 | " | —CH$_2$—(4-F-phenyl) | " | " | | | $n_D^{23}$ 1.6048 |
| 41 | " | —CH$_2$—(4-CH$_3$-phenyl) | " | " | | | m.p. 75~77 |
| 42 | " | —CH$_2$—(4-OCH$_3$-phenyl) | " | " | | | m.p. 94.5~96.5 |

TABLE 1-continued

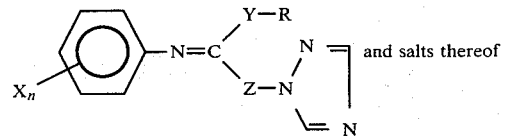 and salts thereof

| Compound No. | $X_n$ | R | Y | Z | Salts Salt-forming component | moles | Refractive index or m.p. (°C.) |
|---|---|---|---|---|---|---|---|
| 43 | " | -CH₂-C₆H₃(Cl)(Cl) (3,4-diCl) | " | " | | | m.p. 94~96 |
| 44 | " | -CH₂-C₆H₃(CH₃)(CH₃) (2,3-diMe) | " | " | | | $n_D^{23}$ 1.6012 |
| 45 | " | -CH₂-C₆H₅ | " | -CH(CH₃)- | | | $n_D^{23}$ 1.6022 |
| 46 | " | -CH₂-C₆H₄-Cl | " | " | | | $n_D^{23}$ 1.6000 |
| 47 | " | -CH₂-C₆H₄-F | " | " | | | m.p. 92~93.5 |
| 48 | " | -CH₂-C₆H₃(Cl)(Cl) | " | " | | | m.p. 56~59 |
| 49 | " | -C₆H₄-Cl | O | -CH₂-CH₂- | | | $n_D^{23}$ 1.6006 |
| 50 | 3-F | -CH₂-C₆H₅ | S | -CH₂- | | | $n_D^{23}$ 1.6014 |
| 51 | " | -CH₂-C₆H₄-Cl | " | " | | | $n_D^{23}$ 1.5985 |
| 52 | " | -i-C₃H₇ | O | -CH(CH₃)- | | | $n_D^{23}$ 1.5998 |
| 53 | 4-F | -CHC≡CH \| CH₃ | " | -CH₂- | | | $n_D^{23}$ 1.6032 |
| 54 | " | -CH₂-C₆H₅ | S | " | | | $n_D^{23}$ 1.6147 |
| 55 | " | -CH₂-C₆H₄-Cl | " | " | | | m.p. 55~56.5 |
| 56 | 2-Br | -t-C₄H₉ | O | " | | | $n_D^{23}$ 1.6145 |
| 57 | " | -CH₂-C₆H₅ | S | " | | | $n_D^{23}$ 1.6170 |
| 58 | " | -CH₂-C₆H₄-Cl | " | " | | | m.p. 55.5~58 |

TABLE 1-continued $$X_n-\text{phenyl}-N=C(Y-R)-Z-N-N=\text{triazole} \text{ and salts thereof}$$

| Compound No. | $X_n$ | R | Y | Z | Salt-forming component | moles | Refractive index or m.p. (°C.) |
|---|---|---|---|---|---|---|---|
| 59 | " | —C₆H₅ | " | —CH₂—CH₂— | | | $n_D^{23}$ 1.6036 |
| 60 | 2-I | —C₂H₅ | O | —CH₂— | | | $n_D^{23}$ 1.6121 |
| 61 | " | —CH₂—C₆H₅ | S | " | | | $n_D^{23}$ 1.6098 |
| 62 | 2-CH₃ | —CH₂—C₆H₅ | " | " | | | $n_D^{23}$ 1.6153 |
| 63 | " | —CH₂—C₆H₄—Cl | " | " | | | $n_D^{23}$ 1.6174 |
| 64 | " | —CH₂CH₂OC₂H₅ | O | —CH(i-C₃H₇)— | | | $n_D^{23}$ 1.6114 |
| 65 | 4-CH₃ | —C₂H₅ | S | —CH₂— | | | $n_D^{23}$ 1.5889 |
| 66 | " | " | " | " | C₆H₅—SO₃H | 1 | m.p. 68~71 (dec) |
| 67 | " | —CH₂—C₆H₅ | " | " | | | $n_D^{23}$ 1.6193 |
| 68 | " | —CH₂CH₂—C₆H₅ | O | —CH(CH₃)— | | | $n_D^{23}$ 1.6274 |
| 69 | 4-n-C₄H₉ | —CH₂—C₆H₄—CN | " | —CH₂— | | | $n_D^{23}$ 1.6185 |
| 70 | " | —CH₃ | S | " | | | $n_D^{23}$ 1.6124 |
| 71 | " | —CH₂CH=CH₂ | " | " | | | $n_D^{23}$ 1.6115 |
| 72 | 2-CH₃O | —CH₂—C₆H₄—Cl | " | " | | | $n_D^{23}$ 1.6202 |
| 73 | " | —CH₂—C₆H₃(Cl)(C₂H₅) | O | —CH(n-C₃H₇)— | | | $n_D^{23}$ 1.6274 |
| 74 | " | —t-C₄H₉ | S | " | | | $n_D^{23}$ 1.6215 |
| 75 | 4-CH₃O | —C₆H₁₁(H) | O | —CH₂— | | | $n_D^{23}$ 1.6226 |
| 76 | " | —C₂H₅ | S | " | | | m.p. 86~88 |
| 77 | " | " | " | " | H₂SO₄ | 1 | m.p. 106~109 |
| 78 | " | —CH₂—C₆H₅ | " | " | | | $n_D^{23}$ 1.6159 |
| 79 | " | —CH₂—C₆H₃(Cl)(Br) | O | —CH(CH₃)— | | | $n_D^{23}$ 1.6036 |

TABLE 1-continued

Structure: Xn-phenyl-N=C(Y-R)(Z-N-N=CH-N ring) and salts thereof

| Compound No. | $X_n$ | R | Y | Z | Salt-forming component | moles | Refractive index or m.p. (°C.) |
|---|---|---|---|---|---|---|---|
| 80 | 3-i-C$_3$H$_7$O | —C$_2$H$_5$ | " | —CH$_2$— | | | $n_D^{23}$ 1.6081 |
| 81 | " | —CH(C$_2$H$_5$)—C$_6$H$_4$—Cl | " | " | | | $n_D^{23}$ 1.6024 |
| 82 | " | —CH$_2$—C$_6$H$_5$ | S | " | | | $n_D^{23}$ 1.5999 |
| 83 | " | —CH$_2$—C$_6$H$_4$—Cl | " | " | | | $n_D^{23}$ 1.6033 |
| 84 | 4-CH$_3$S— | —CH$_2$—C$_6$H$_4$—Cl (meta) | O | " | | | $n_D^{23}$ 1.6115 |
| 85 | " | —CH$_2$CH$_2$OC$_2$H$_5$ | S | " | | | $n_D^{23}$ 1.6111 |
| 86 | " | —n-C$_3$H$_7$ | " | —CH(CH$_3$)—CH$_2$— | | | $n_D^{23}$ 1.6106 |
| 87 | 3-C$_2$H$_5$SO— | —i-C$_3$H$_7$ | " | —CH$_2$— | | | $n_D^{23}$ 1.6008 |
| 88 | " | —CH$_2$—C$_6$H$_3$(Cl)(F) | " | " | | | $n_D^{23}$ 1.6094 |
| 89 | 4-CH$_3$SO$_2$— | —CH$_2$—C$_6$H$_4$—OCH$_3$ | O | " | | | $n_D^{23}$ 1.6154 |
| 90 | " | —n-C$_4$H$_9$ | S | " | | | $n_D^{23}$ 1.6135 |
| 91 | " | —CH$_2$—C$_6$H$_3$(CN)(Cl) | " | " | | | $n_D^{23}$ 1.6175 |
| 92 | 2-CF$_3$ | —CH$_2$—C$_6$H$_5$ | " | " | | | $n_D^{23}$ 1.5816 |
| 93 | " | —CH$_2$—C$_6$H$_4$—Cl | " | " | | | m.p. 87~89 |
| 94 | " | —C$_6$H$_4$—Cl | O | —CH(CH$_3$)— | | | $n_D^{23}$ 1.5946 |
| 95 | " | —CH$_2$—C$_6$H$_3$(CH$_3$)$_2$ | " | —CH(i-C$_3$H$_7$)— | | | $n_D^{23}$ 1.5932 |
| 96 | 4-CF$_3$ | —C$_2$H$_5$ | S | —CH$_2$— | | | $n_D^{23}$ 1.5452 |
| 97 | " | —CH$_2$—C$_6$H$_5$ | " | " | | | m.p. 100~103 |

TABLE 1-continued

| Compound No. | $X_n$ | R | Y | Z | Salts Salt-forming component | moles | Refractive index or m.p. (°C.) |
|---|---|---|---|---|---|---|---|
| 98 | " | —C₆H₅ (phenyl with H) | " | —CH(n-C₄H₉)— | | | $n_D^{23}$ 1.5876 |
| 99 | 4-NO₂ | —n-C₃H₇ | O | —CH₂— | | | $n_D^{23}$ 1.6043 |
| 100 | " | —CH₂CH₂—C₆H₅ | S | " | | | $n_D^{23}$ 1.6085 |
| 101 | " | —CH₂—(3-Cl-C₆H₄) | " | " | | | $n_D^{23}$ 1.6074 |
| 102 | 4-CN | —n-C₄H₉ | O | " | | | $n_D^{23}$ 1.6111 |
| 103 | " | —CH₂—(3,5-Cl₂-C₆H₃) | S | " | | | $n_D^{23}$ 1.6093 |
| 104 | 2,3-Cl₂ | —CH₂—(2-Cl-C₆H₄) | O | " | | | $n_D^{23}$ 1.6125 |
| 105 | " | —C₂H₅ | S | " | | | m.p. 50.5~53 |
| 106 | 2,4-Cl₂ | —CH₃ | O | " | | | $n_D^{23}$ 1.5753 |
| 107 | " | —CH₂CH=CH₂ | " | " | | | $n_D^{23}$ 1.5895 |
| 108 | " | —C₆H₅ | " | " | | | $n_D^{23}$ 1.5896 |
| 109 | " | " | " | " | NiCl₂ | 2 | m.p. 130~133 |
| 110 | " | —CH₃ | S | " | | | $n_D^{23}$ 1.6190 |
| 111 | " | —C₂H₅ | " | " | | | m.p. 65.5~68 |
| 112 | " | " | " | " | p-TsOH | 1 | m.p. 130~133 |
| 113 | " | —n-C₃H₇ | " | " | | | $n_D^{23}$ 1.5954 |
| 114 | " | —i-C₃H₇ | " | " | | | $n_D^{23}$ 1.5818 |
| 115 | " | —n-C₄H₉ | " | " | | | m.p. 55~56.5 |
| 116 | " | —CH₂CH=CH₂ | " | " | | | $n_D^{23}$ 1.6223 |
| 117 | " | —C₆H₅ (with H) | " | " | | | $n_D^{23}$ 1.5924 |
| 118 | " | —C₆H₅ | " | " | | | m.p. 91.5~93.5 |
| 119 | " | " | " | " | CoCl₂ | 2 | m.p. 162~164 |
| 120 | " | —C₆H₄—Cl | " | " | | | $n_D^{23}$ 1.6391 |
| 121 | " | —CH₂—C₆H₅ | " | " | | | m.p. 88~89 |

TABLE 1-continued $$\text{X}_n\text{-}\phantom{a}\text{N}=\text{C}\begin{smallmatrix}Y-R\\Z-N\end{smallmatrix}\begin{smallmatrix}N\\N\end{smallmatrix}\text{ and salts thereof}$$

| Compound No. | $X_n$ | R | Y | Z | Salts Salt-forming component | moles | Refractive index or m.p. (°C.) |
|---|---|---|---|---|---|---|---|
| 122 | " | —CH$_2$—C$_6$H$_4$—Cl (o-Cl) | " | " | | | m.p. 91~93 |
| 123 | " | —CH$_2$—C$_6$H$_4$—Cl (p-Cl) | " | " | | | m.p. 88~90 |
| 124 | " | —CH$_2$—C$_6$H$_4$—F | " | " | | | m.p. 100~101.5 |
| 125 | " | —CH$_2$—C$_6$H$_4$—CH$_3$ | " | " | | | m.p. 83~85 |
| 126 | " | —CH$_2$—C$_6$H$_4$—t-C$_4$H$_9$ | " | " | | | $n_D^{23}$ 1.6088 |
| 127 | " | —CH$_2$—C$_6$H$_4$—OCH$_3$ | " | " | | | m.p. 77~79 |
| 128 | " | —CH$_2$—C$_6$H$_4$—NO$_2$ | " | " | | | m.p. 101~103.5 |
| 129 | " | —CH$_2$—C$_6$H$_3$(Cl)$_2$ (2,4-Cl) | " | " | | | m.p. 115~117 |
| 130 | " | " | " | " | HCl | 1 | m.p. 158~160 |
| 131 | " | —CH$_2$—C$_6$H$_3$(Cl)$_2$ (2,3-Cl) | " | " | | | m.p. 94~96.5 |
| 132 | " | —CH$_2$—C$_6$H$_3$(CH$_3$)$_2$ | " | " | | | m.p. 85~88 |
| 133 | " | —CH(CH$_3$)—C$_6$H$_5$ | " | " | | | $n_D^{23}$ 1.6099 |
| 134 | " | —CH$_2$CH$_2$—C$_6$H$_5$ | " | " | | | $n_D^{23}$ 1.6145 |
| 135 | " | —C$_2$H$_5$ | O | —CH(CH$_3$)— | | | $n_D^{23}$ 1.6021 |
| 136 | " | —CH$_2$CH$_2$OC$_2$H$_5$ | " | " | | | $n_D^{23}$ 1.6114 |
| 137 | " | —CH$_2$—C$_6$H$_4$—F | " | " | | | $n_D^{23}$ 1.6036 |
| 138 | " | —CH$_3$ | S | " | | | m.p. 65~67 |
| 139 | " | —C$_2$H$_5$ | " | " | | | $n_D^{23}$ 1.5950 |

TABLE 1-continued $$\text{X}_n-\phi-N=C\underset{Z-N}{\overset{Y-R}{\diagup}}N=\hspace{-2pt}\diagdown N \quad \text{and salts thereof}$$

| Compound No. | $X_n$ | R | Y | Z | Salts Salt-forming component | moles | Refractive index or m.p. (°C.) |
|---|---|---|---|---|---|---|---|
| 140 | " | —n-C$_3$H$_7$ | " | " | | | $n_D^{23}$ 1.5880 |
| 141 | " | —CH$_2$—⌬ | " | " | | | m.p. 66~68 |
| 142 | " | —CH$_2$—⌬—Cl | " | " | | | m.p. 77~78.5 |
| 143 | " | " | " | " | ⌬—SO$_3$H | 1 | m.p. 102~104 |
| 144 | " | —CH$_2$—⌬—F | " | " | | | $n_D^{23}$ 1.6031 |
| 145 | " | —CH$_2$—⌬—CH$_3$ | " | " | | | m.p. 75.5~78 |
| 146 | " | —CH$_2$—⌬(Cl)(Cl) | " | " | | | $n_D^{23}$ 1.6198 |
| 147 | " | —CH$_2$—⌬(CH$_3$)(CH$_3$) | " | " | | | $n_D^{23}$ 1.5815 |
| 148 | " | —i-C$_3$H$_7$ | O | —CH(C$_2$H$_5$)— | | | $n_D^{23}$ 1.6105 |
| 149 | " | ⌬(Cl)(Cl) | " | " | | | $n_D^{23}$ 1.6023 |
| 150 | " | —CH$_2$—⌬(Cl)(Cl) | " | " | | | $n_D^{23}$ 1.6048 |
| 151 | " | —C$_2$H$_5$ | S | " | | | $n_D^{23}$ 1.6015 |
| 152 | " | —CH$_2$—⌬ | " | " | | | $n_D^{23}$ 1.6084 |
| 153 | " | —CH$_2$—⌬—Cl | " | " | | | $n_D^{23}$ 1.6143 |
| 154 | " | —CH$_2$—⌬ | " | —CH(n-C$_3$H$_7$)— | | | $n_D^{23}$ 1.6071 |
| 155 | " | —CH$_2$—⌬—Cl | " | " | | | $n_D^{23}$ 1.6034 |
| 156 | " | " | " | —CH(sec-C$_4$H$_9$)— | | | $n_D^{23}$ 1.6056 |

TABLE 1-continued

Structure: X_n-phenyl-N=C(Y-R)-Z-N-N=CH-N (tetrazole/triazole) and salts thereof

| Compound No. | $X_n$ | R | Y | Z | Salt-forming component | moles | Refractive index or m.p. (°C.) |
|---|---|---|---|---|---|---|---|
| 157 | 2,5-Cl$_2$ | 3,5-Cl$_2$-4-F-phenyl | O | —CH$_2$— | | | $n_D^{23}$ 1.6087 |
| 158 | " | —C$_2$H$_5$ | S | " | | | $n_D^{23}$ 1.6037 |
| 159 | 2,6-Cl$_2$ | —CH$_2$-(2-S-n-C$_3$H$_7$-phenyl) | O | " | | | $n_D^{23}$ 1.6006 |
| 160 | " | —C$_2$H$_5$ | S | " | | | $n_D^{23}$ 1.5560 |
| 161 | 3,4-Cl$_2$ | —C$_2$H$_5$ | " | " | | | $n_D^{23}$ 1.6134 |
| 162 | " | —CH$_2$-phenyl | " | " | | | $n_D^{23}$ 1.6299 |
| 163 | " | " | " | " | FeCl$_2$ | 2 | m.p. 70~72 (dec) |
| 164 | " | —CH$_2$-(4-Cl-phenyl) | O | —CH(CH$_3$)— | | | $n_D^{23}$ 1.6220 |
| 165 | 3,5-Cl$_2$ | —CH$_2$-(4-SO$_2$CH$_3$-phenyl) | " | —CH$_2$— | | | $n_D^{23}$ 1.6193 |
| 166 | " | —C$_2$H$_5$ | S | " | | | $n_D^{23}$ 1.6023 |
| 167 | " | —CH$_2$-phenyl | " | " | | | $n_D^{23}$ 1.6223 |
| 168 | " | —CH$_2$-(4-Cl-phenyl) | " | " | | | $n_D^{23}$ 1.6274 |
| 169 | 2,4-F$_2$ | cyclohexyl | O | " | | | $n_D^{23}$ 1.5995 |
| 170 | " | —CH$_2$-phenyl | S | " | | | $n_D^{23}$ 1.5983 |
| 171 | " | —CH$_2$-(4-Cl-phenyl) | " | " | | | $n_D^{23}$ 1.5990 |
| 172 | " | —CH$_2$-(2,4-Cl$_2$-phenyl) | " | " | | | m.p. 94~96 |
| 173 | " | —CH$_2$-(3-Cl-5-CN-phenyl) | O | —CH(CH$_3$)— | | | $n_D^{23}$ 1.5994 |
| 174 | 2,4-Br$_2$ | —C$_2$H$_5$ | S | —CH$_2$— | | | $n_D^{23}$ 1.6009 |
| 175 | " | —CH$_2$-phenyl | " | " | | | m.p. 99.5~101 |

TABLE 1-continued

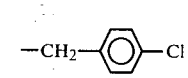 and salts thereof

| Compound No. | $X_n$ | R— | Y | Z | Salts Salt-forming component | moles | Refractive index or m.p. (°C.) |
|---|---|---|---|---|---|---|---|
| 176 | " | " | " | " | CuSO₄ | 2 | m.p. 101~103 (dec) |
| 177 | " | —CH₂—⟨C₆H₄⟩—Cl | " | " | | | m.p. 92.5~94 |
| 178 | 2-Cl, 4-Br | —C₂H₅ | O | " | | | $n_D^{23}$ 1.6198 |
| 179 | " | —CH₃ | S | " | | | $n_D^{23}$ 1.6310 |
| 180 | " | —C₂H₅ | " | " | | | $n_D^{23}$ 1.6295 |
| 181 | " | —n-C₃H₇ | " | " | | | $n_D^{23}$ 1.6274 |
| 182 | " | —CH₂—⟨C₆H₅⟩ | " | " | | | m.p. 103~104 |
| 183 | " | —CH₂—⟨C₆H₄⟩—Cl | " | " | | | m.p. 85.5~88.5 |
| 184 | " | —CH(CH₃)—⟨C₆H₅⟩ | O | —CH(CH₃)— | | | $n_D^{23}$ 1.6221 |
| 185 | " | —CH₂—⟨C₆H₅⟩ | S | " | | | $n_D^{23}$ 1.6195 |
| 186 | 2-Br, 4-Cl | —CH₂—⟨C₆H₃⟩(Cl)(Cl) | O | —CH₂— | | | $n_D^{23}$ 1.6231 |
| 187 | " | —CH₃ | S | " | | | $n_D^{23}$ 1.6105 |
| 188 | " | —C₂H₅ | " | " | | | m.p. 55.5~57 |
| 189 | " | —n-C₃H₇ | " | " | | | $n_D^{23}$ 1.6070 |
| 190 | " | —CH₂—⟨C₆H₅⟩ | " | " | | | m.p. 77~78.5 |
| 191 | " | " | " | " | HCl | 1 | m.p. 128~131 |
| 192 | " | —CH₂—⟨C₆H₄⟩—Cl | " | " | | | m.p. 70~72 |
| 193 | " | —CH₂—⟨C₆H₅⟩ | O | —CH(CH₃)— | | | $n_D^{23}$ 1.6098 |
| 194 | " | —CH₂CH=CH₂ | " | —CH(i-C₄H₉)— | | | $n_D^{23}$ 1.6152 |
| 195 | 2-Cl, 4-F | —CH₃ | " | —CH₂— | | | $n_D^{23}$ 1.6148 |
| 196 | " | ⟨C₆H₄⟩—Cl | " | " | | | $n_D^{23}$ 1.6088 |
| 197 | " | —CH₂—⟨C₆H₅⟩ | " | " | | | $n_D^{23}$ 1.6137 |
| 198 | " | —CH₃ | S | " | | | m.p. 108~110 |
| 199 | " | —C₂H₅ | " | " | | | m.p. 87~90 |
| 200 | " | —n-C₃H₇ | " | " | | | $n_D^{23}$ 1.5716 |

TABLE 1-continued general structure: $X_n$-phenyl-$N=C(Y-R)(Z-N)$-pyrazole/triazole "and salts thereof"

| Compound No. | $X_n$ | R | Y | Z | Salt-forming component | moles | Refractive index or m.p. (°C.) |
|---|---|---|---|---|---|---|---|
| 201 | " | —CH₂—C₆H₅ | " | " | | | $n_D^{23}$ 1.6115 |
| 202 | " | —CH₂—C₆H₄—Cl (o) | " | " | | | m.p. 76~77.5 |
| 203 | " | —CH₂—C₆H₄—Cl (m) | " | " | | | $n_D^{23}$ 1.6065 |
| 204 | " | —CH₂—C₆H₄—Cl (p) | " | " | | | m.p. 59~61 |
| 205 | " | " | " | " | (CO₂H)₂ | 1 | m.p. 143~145 |
| 206 | " | —CH₂—C₆H₄—F | " | " | | | m.p. 45~48 |
| 207 | " | —CH₂—C₆H₄—CH₃ | " | " | | | m.p. 48~50 |
| 208 | " | —CH₂—C₆H₄—OCH₃ | " | " | | | $n_D^{23}$ 1.6003 |
| 209 | " | —CH₂—C₆H₃—Cl₂ (2,3) | " | " | | | m.p. 109~111 |
| 210 | " | —CH₂—C₆H₃—Cl₂ | " | " | | | m.p. 72~75 |
| 211 | " | —CH₂—C₆H₃—(CH₃)₂ | " | " | | | m.p. 79~81 |
| 212 | " | —t-C₄H₉ | O | —CH(CH₃)— | | | $n_D^{23}$ 1.6006 |
| 213 | " | —CH₂—C₆H₅ | S | " | | | $n_D^{23}$ 1.6142 |
| 214 | " | —CH₂—C₆H₄—Cl | " | " | | | $n_D^{23}$ 1.6039 |
| 215 | " | —CH₂—C₆H₄—F | " | " | | | $n_D^{23}$ 1.6117 |

TABLE 1-continued

[Structure: X_n-phenyl-N=C(Y-R)(Z-N-N=)-triazole and salts thereof]

| Compound No. | $X_n$ | R | Y | Z | Salts Salt-forming component | moles | Refractive index or m.p. (°C.) |
|---|---|---|---|---|---|---|---|
| 216 | " | —CH₂—(2,4-Cl₂-phenyl) | " | " | | | m.p. 105.5~108 |
| 217 | " | —CH₂—(phenyl) | " | —CH(C₂H₅)— | | | $n_D^{23}$ 1.5901 |
| 218 | " | —CH₂—(4-Cl-phenyl) | " | " | | | m.p. 79.5~81 |
| 219 | " | —CH₂—(phenyl) | " | —CH(n-C₃H₇)— | | | $n_D^{23}$ 1.5787 |
| 220 | " | —CH₂—(4-Cl-phenyl) | " | " | | | $n_D^{23}$ 1.5875 |
| 221 | 2-F, 4-Cl | —CH₃ | O | —CH₂— | | | $n_D^{23}$ 1.6075 |
| 222 | " | —CH(CH₃)—C≡CH | " | " | | | $n_D^{23}$ 1.6109 |
| 223 | " | —CH₃ | S | " | | | m.p. 82~84 |
| 224 | " | " | " | " | 3,5-dinitro-2-CO₂H benzoic acid | 1 | m.p. 84~86 |
| 225 | " | —C₂H₅ | " | " | | | m.p. 60~63 |
| 226 | " | —n-C₃H₇ | " | " | | | $n_D^{23}$ 1.6040 |
| 227 | " | —CH₂—(phenyl) | " | " | | | m.p. 57~58.5 |
| 228 | " | —CH₂—(4-Cl-phenyl) | " | " | | | m.p. 102~103.5 |
| 229 | " | —CH₂—(4-F-phenyl) | " | " | | | m.p. 62~64 |
| 230 | " | —CH₂—(4-CH₃-phenyl) | " | " | | | $n_D^{23}$ 1.6071 |
| 231 | " | —CH₂—(4-OCH₃-phenyl) | " | " | | | $n_D^{23}$ 1.6104 |
| 232 | " | —CH₂—(2,3-Cl₂-phenyl) | " | " | | | m.p. 116.5~119 |
| 233 | " | —CH₂—(2,3-Cl₂-phenyl) | " | " | | | m.p. 104~106 |

TABLE 1-continued

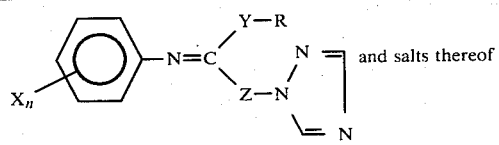 and salts thereof

| Compound No. | $X_n$ | R | Y | Z | Salts Salt-forming component | moles | Refractive index or m.p. (°C.) |
|---|---|---|---|---|---|---|---|
| 234 | " | −CH₂−C₆H₃(CH₃)(CH₃) (2,4-diMe benzyl) | " | " | | | m.p. 102.5~105.5 |
| 235 | " | −CH₂−C₆H₄−CH₃ | O | −CH(CH₃)− | | | $n_D^{23}$ 1.6025 |
| 236 | " | −CH₂−C₆H₄−Cl | S | " | | | $n_D^{23}$ 1.6114 |
| 237 | " | −C₆H₅ | " | −CH₂−CH(CH₃)− | | | $n_D^{23}$ 1.6095 |
| 238 | 2-Cl, 4-I | −C₆H₄−Cl | O | −CH₂− | | | $n_D^{23}$ 1.6006 |
| 239 | " | −n-C₄H₉ | S | " | | | $n_D^{23}$ 1.5973 |
| 240 | " | −CH₂−C₆H₂(Cl)(Cl)(Cl) (2,4,5-triCl benzyl) | " | " | | | $n_D^{23}$ 1.5980 |
| 241 | 2,4-(CH₃)₂ | −C₂H₅ | " | " | | | $n_D^{23}$ 1.5791 |
| 242 | " | −CH₂−C₆H₅ | " | " | | | m.p. 47~50 |
| 243 | " | −C₆H₅ | O | −(CH₂)₃− | | | $n_D^{23}$ 1.5820 |
| 244 | 2,6-(CH₃)₂ | −CH₂CH₂−C₆H₁₁ | " | −CH₂− | | | $n_D^{23}$ 1.5907 |
| 245 | " | −C₂H₅ | S | " | | | $n_D^{23}$ 1.5778 |
| 246 | " | −CH₂−C₆H₅ | " | " | | | $n_D^{23}$ 1.6074 |
| 247 | " | −CH₂−C₆H₄−Cl | " | " | | | $n_D^{23}$ 1.6085 |
| 248 | " | " | " | " | NiCl₂ | 2 | m.p. 176~178 |
| 249 | " | −CH₂−C₆H₃(Cl)(Cl) (2,4-diCl benzyl) | " | " | | | $n_D^{23}$ 1.6104 |
| 250 | " | −CH₂−C₆H₃(CH₃)(CH₃) (2,4-diMe benzyl) | " | " | | | m.p. 103~104 |

TABLE 1-continued $$\underset{X_n}{\phantom{XX}}\text{-phenyl-N=C}\underset{Z-N}{\overset{Y-R}{<}}\text{N-N=CH-N (ring)} \text{ and salts thereof}$$

| Compound No. | $X_n$ | R | Y | Z | Salt-forming component | moles | Refractive index or m.p. (°C.) |
|---|---|---|---|---|---|---|---|
| 251 | " | —CH$_2$—(3-Cl, 4-SO$_2$CH$_3$-phenyl) | " | —CH(n-C$_4$H$_9$)— | | | $n_D^{23}$ 1.5993 |
| 252 | 2-Me, 4-Cl | —CH$_2$—phenyl | O | —CH$_2$— | | | $n_D^{23}$ 1.5941 |
| 253 | " | —C$_2$H$_5$ | S | " | | | $n_D^{23}$ 1.5959 |
| 254 | " | —t-C$_4$H$_9$ | " | " | | | $n_D^{23}$ 1.6036 |
| 255 | 2-Cl, 4-CH$_3$O | —C$_2$H$_5$ | " | " | | | $n_D^{23}$ 1.6003 |
| 256 | " | —CH(C$_2$H$_5$)—phenyl | " | " | | | $n_D^{23}$ 1.6084 |
| 257 | " | —CH$_2$CH$_2$SCH$_3$ | O | —CH(CH$_3$)— | | | $n_D^{23}$ 1.6110 |
| 258 | " | —CH$_2$—(3-SOC$_2$H$_5$-phenyl) | S | " | | | $n_D^{23}$ 1.6092 |
| 259 | " | —CH$_2$—(2-Cl, 3-CF$_3$-phenyl) | " | —CH(n-C$_3$H$_7$)— | | | $n_D^{23}$ 1.6145 |
| 260 | 2-Br, 4-CH$_3$SO$_2$— | —CH$_2$—(4-t-C$_4$H$_9$-phenyl) | O | —CH$_2$— | | | $n_D^{23}$ 1.6082 |
| 261 | " | —CH(CH$_3$)C≡CH | S | " | | | $n_D^{23}$ 1.6009 |
| 262 | " | —(3,4-diCl-phenyl) | " | " | | | $n_D^{23}$ 1.6035 |
| 263 | 2-Cl, 4-CF$_3$ | —CH$_2$—(4-F-phenyl) | O | " | | | $n_D^{23}$ 1.5877 |
| 264 | " | —C$_2$H$_5$ | S | " | | | $n_D^{23}$ 1.5957 |
| 265 | " | —CH$_2$—phenyl | " | " | | | m.p. 93~95 |
| 266 | " | " | " | " | H$_2$SO$_4$ | 1 | m.p. 149~150.5 |
| 267 | " | —CH$_2$—(4-Cl-phenyl) | " | " | | | m.p. 91~92.5 |
| 268 | " | —CH$_2$—(4-F-phenyl) | " | " | | | m.p. 96~98 |

TABLE 1-continued

Structure: aryl(X_n)-N=C with Y-R and Z-N bridging to a pyrazole-like ring, and salts thereof

| Compound No. | $X_n$ | R | Y | Z | Salt-forming component | moles | Refractive index or m.p. (°C.) |
|---|---|---|---|---|---|---|---|
| 269 | " | −CH₂−(3-F,4-Cl-phenyl) | O | −CH(CH₃)− | | | $n_D^{23}$ 1.5886 |
| 270 | 2-CF₃, 4-Cl | −n-C₃H₇ | " | −CH₂− | | | $n_D^{23}$ 1.5711 |
| 271 | " | −cyclopentyl(H) | " | " | | | $n_D^{23}$ 1.5639 |
| 272 | " | −CH₂−(4-Cl-phenyl) | " | " | | | $n_D^{23}$ 1.5521 |
| 273 | " | −CH₃ | S | " | | | $n_D^{23}$ 1.5628 |
| 274 | " | −C₂H₅ | " | " | | | $n_D^{23}$ 1.5563 |
| 275 | " | −n-C₃H₇ | " | " | | | $n_D^{23}$ 1.5552 |
| 276 | " | −i-C₃H₇ | " | " | | | $n_D^{23}$ 1.5474 |
| 277 | " | −n-C₄H₉ | " | " | | | m.p. 54~55.5 |
| 278 | " | −CH₂CH=CH₂ | " | " | | | $n_D^{23}$ 1.5451 |
| 279 | " | −CH₂−phenyl | " | " | | | m.p. 59~61 |
| 280 | " | −CH₂−(4-Cl-phenyl) | " | " | | | m.p. 45.5~48 |
| 281 | " | " | " | " | (CO₂H)₂ | 1 | m.p. 200~202 |
| 282 | " | −CH₂−(4-F-phenyl) | " | " | | | m.p. 49~50.5 |
| 283 | " | −CH₂−(4-CH₃-phenyl) | " | " | | | m.p. 60.5~62 |
| 284 | " | −CH₂−(3,4-diCl-phenyl) | " | " | | | m.p. 98.5~100 |
| 285 | " | −CH₂−(3,4-diCH₃-phenyl) | " | " | | | m.p. 58~60 |
| 286 | " | −CH₃ | O | −CH(CH₃)− | | | $n_D^{23}$ 1.5605 |
| 287 | " | −CH₂−(4-Cl-phenyl) | " | " | | | $n_D^{23}$ 1.5573 |
| 288 | " | −CH₃ | S | " | | | $n_D^{23}$ 1.5541 |
| 289 | " | −C₂H₅ | " | " | | | $n_D^{23}$ 1.5501 |
| 290 | " | −n-C₃H₇ | " | " | | | $n_D^{23}$ 1.5397 |
| 291 | " | " | " | " | p-TsOH | 1 | m.p. 102~105 |
| 292 | " | −CH₂−phenyl | " | " | | | $n_D^{23}$ 1.5779 |

TABLE 1-continued

| Compound No. | $X_n$ | R | Y | Z | Salts Salt-forming component | moles | Refractive index or m.p. (°C.) |
|---|---|---|---|---|---|---|---|
| 293 | " | $-CH_2-\text{C}_6H_4-Cl$ | " | " | | | $n_D^{23}$ 1.5663 |
| 294 | " | $-CH_2-\text{C}_6H_3(Cl)(Cl)$ | " | " | | | m.p. 94~96 |
| 295 | " | $-CH_2-\text{C}_6H_3(CH_3)(CH_3)$ | " | " | | | $n_D^{23}$ 1.5741 |
| 296 | " | $-CH_2-\text{C}_6H_5$ | " | $-CH(C_2H_5)-$ | | | $n_D^{23}$ 1.5761 |
| 297 | " | $-CH_2-\text{C}_6H_4-Cl$ | " | " | | | $n_D^{23}$ 1.5795 |
| 298 | " | $-CH_2-\text{C}_6H_5$ | " | $-CH(n-C_3H_7)-$ | | | $n_D^{23}$ 1.5706 |
| 299 | " | $-CH_2-\text{C}_6H_4-Cl$ | " | " | | | $n_D^{23}$ 1.5710 |
| 300 | 2-CH$_3$, 4-CF$_3$ | $-C_2H_5$ | " | $-CH_2-$ | | | $n_D^{23}$ 1.5621 |
| 301 | " | $-CH_2-\text{C}_6H_5$ | " | " | | | $n_D^{23}$ 1.5830 |
| 302 | " | $-CH_2-\text{C}_6H_4-Cl$ | " | " | | | $n_D^{23}$ 1.5776 |
| 303 | 2-CH$_3$, 6-NO$_2$ | $-CH_2-\text{C}_6H_5$ | " | " | | | $n_D^{23}$ 1.6053 |
| 304 | " | $-CH_2-\text{C}_6H_4-Cl$ | " | " | | | $n_D^{23}$ 1.6115 |
| 305 | " | $-n-C_4H_9$ | O | $-CH(CH_3)-$ | | | $n_D^{23}$ 1.6097 |
| 306 | " | $-CH_2-\text{C}_6H_4-SO_2CH_3$ | S | " | | | $n_D^{23}$ 1.6131 |
| 307 | 2-CH$_3$, 4-CN | $-i-C_3H_7$ | O | $-CH_2-$ | | | $n_D^{23}$ 1.6129 |
| 308 | " | $-CH_2-\text{C}_6H_3(Br)(Cl)$ | S | " | | | $n_D^{23}$ 1.6086 |
| 309 | 2,3,4-Cl$_3$ | $-CH_2CH_2OC_2H_5$ | O | " | | | $n_D^{23}$ 1.6104 |
| 310 | " | $-C_2H_5$ | S | " | | | m.p. 87.5~89.5 |

TABLE 1-continued

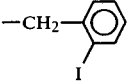 and salts thereof

| Compound No. | $X_n$ | R | Y | Z | Salts Salt-forming component | moles | Refractive index or m.p. (°C.) |
|---|---|---|---|---|---|---|---|
| 311 | " | —CH$_2$—(2-I-C$_6$H$_4$) | " | " | | | $n_D^{23}$ 1.6121 |
| 312 | 2,4,5-Cl$_3$ | —CH$_2$CH$_2$—(2,4-Cl$_2$-3-CH$_3$-C$_6$H$_2$) | O | " | | | $n_D^{23}$ 1.6076 |
| 313 | " | —C$_2$H$_5$ | S | " | | | $n_D^{23}$ 1.6208 |
| 314 | " | " | " | " | CuCl$_2$ | 2 | m.p. 121~122.5 |
| 315 | " | —CH$_2$—C$_6$H$_5$ | " | " | | | $n_D^{23}$ 1.6111 |
| 316 | " | —CH$_2$—(4-Cl-C$_6$H$_4$) | " | " | | | m.p. 109~110.5 |
| 317 | " | —C$_6$H$_5$ | O | —CH(i-C$_4$H$_9$)— | | | $n_D^{23}$ 1.6031 |
| 318 | 2,4,6-Cl$_3$ | —CH(CH$_3$)—C≡CH | " | —CH$_2$— | | | $n_D^{23}$ 1.5946 |
| 319 | " | —C$_2$H$_5$ | S | " | | | $n_D^{23}$ 1.5756 |
| 320 | " | —CH$_2$—(5-CH$_3$-3-NO$_2$-C$_6$H$_3$) | " | " | | | $n_D^{23}$ 1.5898 |
| 321 | 2,4-Cl$_2$, 5-F | —C$_2$H$_5$ | " | " | | | $n_D^{23}$ 1.5941 |
| 322 | " | —i-C$_3$H$_7$ | O | —CH(CH$_3$)— | | | $n_D^{23}$ 1.5976 |
| 323 | " | —CH$_2$CH$_2$SCH$_3$ | S | " | | | $n_D^{23}$ 1.6072 |
| 324 | " | —CH$_2$—(2-S-n-C$_3$H$_7$-C$_6$H$_4$) | " | " | | | $n_D^{23}$ 1.6008 |
| 325 | 2,4-Cl$_2$, 5-CF$_3$ | —C$_2$H$_5$ | O | —CH$_2$— | | | $n_D^{23}$ 1.5994 |
| 326 | " | —C$_6$H$_{11}$ | S | " | | | $n_D^{23}$ 1.5871 |
| 327 | " | —CH$_2$—(3-Cl-C$_6$H$_4$) | " | " | | | $n_D^{23}$ 1.5914 |
| 328 | 2,6-Cl$_2$, 4-CH$_3$O | —CH$_2$—C$_6$H$_5$ | O | " | | | $n_D^{23}$ 1.5989 |

TABLE 1-continued

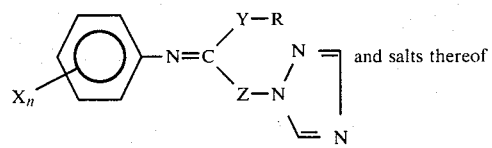

and salts thereof

| Compound No. | $X_n$ | R | Y | Z | Salts Salt-forming component | moles | Refractive index or m.p. (°C.) |
|---|---|---|---|---|---|---|---|
| 329 | " | —C$_2$H$_5$ | S | " | | | $n_D^{23}$ 1.6046 |
| 330 | " | " | " | " | p-TsOH | 1 | m.p. 89~92 |
| 331 | 2,6-Cl$_2$, 4-CH$_3$O | —CH$_2$—⟨◯⟩—CN | " | " | | | $n_D^{23}$ 1.6014 |
| 332 | 2,4-Cl$_2$, 6-CH$_3$O | —C$_2$H$_5$ | " | " | | | $n_D^{23}$ 1.6008 |
| 333 | " | —CH$_2$—⟨◯⟩—C$_2$H$_5$ (Cl) | " | " | | | $n_D^{23}$ 1.6035 |
| 334 | " | —n-C$_4$H$_9$ | O | —CH— CH$_3$ | | | $n_D^{23}$ 1.6109 |

Note:
p-TsOH denotes p-toluenesulfonic acid in the above table.

The following Examples 14 to 19 illustrate the procedures for preparing the fungicidal compositions of this invention but are not limitative of this invention. In Examples 14 to 19 "parts" are given by weight.

EXAMPLE 14

Wettable Powder

20 Parts of Compound No. 123, 5 parts of polyoxyethylene alkylarylethers, 3 parts of calcium ligninsulfonate and 72 parts of diatomaceous earth were mixed together and ground uniformly to give a wettable powder containing 20% by weight of the active ingredient compound.

EXAMPLE 15

Emulsifiable Concentrate

30 Parts of Compound No. 38, 50 parts of xylene and 20 parts of polyoxyethylene alkylarylethers were mixed together to make a uniform dissolution, affording an emulsifiable concentrate containing 30% by weight of the active ingredient compound.

EXAMPLE 16

Oily Formulation

50 Parts of Compound No. 206 and 50 parts of ethyl cellosolve were mixed together to make a uniform dissolution, affording an oily formulation containing 50% by weight of the active ingredient compound.

EXAMPLE 17

Sol (Flowable Powder)

40 Parts of finely divided Compound No. 316 having average particle size of not more than 10 microns, 2 parts of lauryl sulfate, 2 parts of sodium alkylnaphthalenesulfonate, 1 part of hydroxypropylcellulose and 55 parts of water were mixed together uniformly to give a sol containing 40% by weight of the active ingredient compound.

EXAMPLE 18

Dusting Powder 0.5 Parts of Compound No. 280, 0.5 parts of finely divided silica, 0.5 parts of calcium stearate, 50 parts of clay and 48.5 parts of talc were mixed together and ground uniformly to give a dusting powder containing 1% of the active ingredient compound.

EXAMPLE 19

Granules

3 Parts of Compound No. 177, 1 part of calcium ligninsulfonate, 30 parts of bentonite and 66 parts of clay were mixed together and ground uniformly. The powdery mixture obtained was granulated with addition of water, followed by drying and screening. Granules containing 3% of the active ingredient compound were obtained.

EXAMPLE 20

This Example illustrate tests of controlling leaf rust in wheat for preventative treatment.

Wheat plants (variety: Norin No. 61) were grown in soil in 9 cm-diameter porous pots in a greenhouse. At the first true-leaf stage, the wheat seedlings were sprayed with the composition under test which was prepared by diluting the wettable powder of the Example 14 with water to a particular concentration of the active compound indicated in Table 2 below. The rate of application of the composition sprayed was 20 ml per three pots. One day after the treatment, the treated foliage was inoculated with a suspension of uredospores of wheat leaf rust fungi (*Puccinia recondita*) at such inoculum density that the number of uredospores on the slide glass observed within the vision field of a microscope (×150) amounted to approximately 50. The spore suspension used was prepared by suspending the uredospores which were previously produced on another wheat leaves, into a volume of sterilized water containing 50 ppm of a dispersion agent "Tween 20" (a trade name of polyoxyethylene sorbitan monolaurate, a product of Kao Atlas Co., Japan). The inoculated wheat plants were incubated overnight in a high humidity room at 20° C. and then transferred into a greenhouse at 20° C. in which the environment was appropriate to allow the infection to take place. 10 Days after the inoculation, the infected wheat plants were removed out from the greenhouse and estimated for the degree of disease development. To this end, the number of the uredosorus per leaf was assessed and the degree of control (%) was evaluated according to the under-mentioned equation. The degree of phytotoxicity of the test compound to wheat plant was assessed according to the under-mentioned grading. The tests were conducted with three replicates for a particular value of the concentration of the test compound, and the average of the evaluated degree of control (%) was calculated. The test results (expressed as averaged Control (%)) are set out in Table 2 below.

$$\text{Control (\%)} = \left(1 - \frac{\text{Number of uredosorus in treated plot}}{\text{Number of uredosorus in non-treated plant}}\right) \times 100$$

Grades for estimation of phytotoxicity
5—Very much severe
4—Severe
3—Strong
2—Slight
1—Very slight
0—None

EXAMPLE 21

This Example illustrates tests of controlling powdery mildew in cucumber.

Cucumber plants (variety: Sagami-Hanjiro) were grown in soil in 9 cm-diameter porous pots in a greenhouse. At the first true-leaf stage, the cucumber seedlings were sprayed with 10 ml per pot of the composition under test which was prepared by diluting the emulsifiable concentrate of the Example 15 with water to a particular concentration of the active compound indicated in Table 2 below. The treated cucumber plants were allowed to stand overnight and then sprayed for inoculation with a suspension of spores of cucumber powdery mildew fungi (*Sphaerotheca fuliginea*). 10 Days after the inoculation, the rate (%) of the area of the symptom on the infected leaves was assessed, and the degree of control (%) was evaluated according to the under-mentioned equation. The degree of phytotoxicity of the test compound to cucumber plant was estimated by the same grading as in Example 20. The tests were conducted with three replicates. The test results (expressed as averaged % Control) are given in Table 2.

$$\text{Control (\%)} = \left(1 - \frac{\text{Rate of area of symptom in treated plot}}{\text{Rate of area of symptom in non-treated plot}}\right) \times 100$$

TABLE 2

| Compound No. | Control (%) Concentration of active ingredient compound sprayed (ppm) | | Phytotoxicity | |
|---|---|---|---|---|
| | Leaf rust on wheat 50 | Powdery mildew on cucumber 50 | Wheat | Cucumber |
| 1 | 88 | 92 | 0 | 0 |
| 2 | 91 | 96 | " | " |
| 3 | 89 | 100 | " | " |
| 4 | 100 | 100 | " | " |
| 5 | 98 | 100 | " | " |
| 6 | 100 | 84 | " | " |
| 7 | 92 | 83 | " | " |
| 8 | 96 | 83 | " | " |
| 9 | 89 | 84 | " | " |
| 10 | 96 | 86 | " | " |
| 11 | 95 | 99 | " | " |
| 12 | 100 | 94 | " | " |
| 13 | 89 | 89 | " | " |
| 14 | 93 | 99 | " | " |
| 15 | 85 | 89 | " | " |
| 16 | 83 | 86 | " | " |
| 17 | 92 | 100 | " | " |
| 18 | 90 | 87 | " | " |
| 19 | 98 | 100 | " | " |
| 20 | 100 | 100 | " | " |
| 21 | 93 | 85 | " | " |
| 22 | 98 | 87 | " | " |
| 23 | 87 | 100 | " | " |
| 24 | 83 | 89 | " | " |
| 25 | 98 | 88 | " | " |
| 26 | 96 | 90 | " | " |
| 27 | 99 | 94 | " | " |
| 28 | 92 | 98 | " | " |
| 29 | 95 | 94 | " | " |
| 30 | 85 | 88 | " | " |
| 31 | 87 | 86 | " | " |
| 32 | 90 | 89 | " | " |
| 33 | 91 | 100 | " | " |
| 34 | 90 | 88 | " | " |
| 35 | 87 | 88 | " | " |
| 36 | 89 | 89 | " | " |
| 37 | 91 | 83 | " | " |
| 38 | 100 | 100 | " | " |
| 39 | 100 | 99 | " | " |
| 40 | 100 | 83 | " | " |
| 41 | 97 | 88 | " | " |
| 42 | 99 | 86 | " | " |
| 43 | 98 | 83 | " | " |
| 44 | 98 | 86 | " | " |
| 45 | 89 | 85 | " | " |
| 46 | 100 | 86 | " | " |
| 47 | 94 | 85 | " | " |
| 48 | 92 | 90 | " | " |
| 49 | 84 | 87 | " | " |
| 50 | 86 | 83 | " | " |
| 51 | 89 | 83 | " | " |
| 52 | 83 | 88 | " | " |
| 53 | 87 | 90 | " | " |
| 54 | 91 | 83 | " | " |
| 55 | 92 | 83 | " | " |
| 56 | 85 | 84 | " | " |
| 57 | 86 | 86 | " | " |
| 58 | 88 | 89 | " | " |
| 59 | 89 | 91 | " | " |
| 60 | 90 | 96 | " | " |
| 61 | 91 | 90 | " | " |
| 62 | 92 | 83 | " | " |
| 63 | 94 | 85 | " | " |
| 64 | 87 | 86 | " | " |
| 65 | 98 | 83 | " | " |
| 66 | 92 | 84 | " | " |
| 67 | 99 | 96 | " | " |
| 68 | 85 | 90 | " | " |
| 69 | 86 | 91 | " | " |
| 70 | 90 | 86 | " | " |
| 71 | 93 | 85 | " | " |
| 72 | 94 | 83 | " | " |
| 73 | 90 | 98 | " | " |
| 74 | 87 | 96 | " | " |

TABLE 2-continued

| Compound No. | Control (%) Concentration of active ingredient compound sprayed (ppm) | | Phytotoxicity | |
|---|---|---|---|---|
| | Leaf rust on wheat 50 | Powdery mildew on cucumber 50 | Wheat | Cucumber |
| 75 | 92 | 85 | " | " |
| 76 | 87 | 83 | " | " |
| 77 | 85 | 86 | " | " |
| 78 | 87 | 89 | " | " |
| 79 | 92 | 87 | " | " |
| 80 | 94 | 89 | " | " |
| 81 | 88 | 87 | " | " |
| 82 | 99 | 99 | " | " |
| 83 | 100 | 100 | " | " |
| 84 | 85 | 92 | " | " |
| 85 | 85 | 90 | " | " |
| 86 | 84 | 85 | " | " |
| 87 | 83 | 86 | " | " |
| 88 | 89 | 91 | " | " |
| 89 | 84 | 87 | " | " |
| 90 | 85 | 99 | " | " |
| 91 | 90 | 96 | " | " |
| 92 | 86 | 98 | " | " |
| 93 | 88 | 100 | " | " |
| 94 | 92 | 89 | " | " |
| 95 | 93 | 90 | " | " |
| 96 | 98 | 83 | " | " |
| 97 | 85 | 83 | " | " |
| 98 | 87 | 85 | " | " |
| 99 | 91 | 87 | " | " |
| 100 | 93 | 86 | " | " |
| 101 | 96 | 91 | " | " |
| 102 | 92 | 90 | " | " |
| 103 | 89 | 93 | " | " |
| 104 | 96 | 91 | " | " |
| 105 | 85 | 89 | " | " |
| 106 | 100 | 100 | " | " |
| 107 | 94 | 98 | " | " |
| 108 | 88 | 100 | " | " |
| 109 | 86 | 100 | " | " |
| 110 | 96 | 90 | " | " |
| 111 | 100 | 100 | " | " |
| 112 | 98 | 98 | " | " |
| 113 | 97 | 100 | " | " |
| 114 | 90 | 93 | " | " |
| 115 | 95 | 94 | " | " |
| 116 | 94 | 100 | " | " |
| 117 | 88 | 89 | " | " |
| 118 | 93 | 87 | " | " |
| 119 | 95 | 84 | " | " |
| 120 | 90 | 90 | " | " |
| 121 | 100 | 100 | " | " |
| 122 | 89 | 98 | " | " |
| 123 | 100 | 100 | " | " |
| 124 | 98 | 100 | " | " |
| 125 | 98 | 100 | " | " |
| 126 | 86 | 100 | " | " |
| 127 | 100 | 100 | " | " |
| 128 | 97 | 96 | " | " |
| 129 | 99 | 100 | " | " |
| 130 | 98 | 100 | " | " |
| 131 | 86 | 87 | " | " |
| 132 | 100 | 100 | " | " |
| 133 | 83 | 90 | " | " |
| 134 | 90 | 85 | " | " |
| 135 | 99 | 99 | " | " |
| 136 | 96 | 96 | " | " |
| 137 | 98 | 98 | " | " |
| 138 | 92 | 83 | " | " |
| 139 | 89 | 100 | " | " |
| 140 | 87 | 100 | " | " |
| 141 | 100 | 100 | " | " |
| 142 | 100 | 100 | " | " |
| 143 | 100 | 100 | " | " |
| 144 | 98 | 100 | " | " |
| 145 | 100 | 100 | " | " |
| 146 | 100 | 100 | " | " |
| 147 | 99 | 100 | " | " |
| 148 | 89 | 87 | " | " |
| 149 | 91 | 94 | " | " |
| 150 | 90 | 92 | " | " |
| 151 | 98 | 89 | " | " |
| 152 | 100 | 100 | " | " |
| 153 | 100 | 100 | " | " |
| 154 | 97 | 100 | " | " |
| 155 | 100 | 100 | " | " |
| 156 | 98 | 100 | " | " |
| 157 | 92 | 90 | " | " |
| 158 | 87 | 86 | " | " |
| 159 | 91 | 89 | " | " |
| 160 | 85 | 87 | " | " |
| 161 | 83 | 86 | " | " |
| 162 | 87 | 86 | " | " |
| 163 | 90 | 85 | " | " |
| 164 | 86 | 87 | " | " |
| 165 | 98 | 99 | " | " |
| 166 | 97 | 92 | " | " |
| 167 | 91 | 96 | " | " |
| 168 | 94 | 98 | " | " |
| 169 | 86 | 86 | " | " |
| 170 | 99 | 84 | " | " |
| 171 | 100 | 89 | " | " |
| 172 | 97 | 86 | " | " |
| 173 | 90 | 90 | " | " |
| 174 | 94 | 100 | " | " |
| 175 | 99 | 100 | " | " |
| 176 | 97 | 98 | " | " |
| 177 | 100 | 100 | " | " |
| 178 | 83 | 93 | " | " |
| 179 | 91 | 91 | " | " |
| 180 | 86 | 98 | " | " |
| 181 | 92 | 100 | " | " |
| 182 | 100 | 100 | " | " |
| 183 | 100 | 100 | " | " |
| 184 | 87 | 84 | " | " |
| 185 | 100 | 99 | " | " |
| 186 | 91 | 89 | " | " |
| 187 | 93 | 92 | " | " |
| 188 | 89 | 100 | " | " |
| 189 | 98 | 100 | " | " |
| 190 | 100 | 100 | " | " |
| 191 | 100 | 100 | " | " |
| 192 | 100 | 100 | " | " |
| 193 | 97 | 91 | " | " |
| 194 | 90 | 87 | " | " |
| 195 | 94 | 90 | " | " |
| 196 | 98 | 88 | " | " |
| 197 | 100 | 85 | " | " |
| 198 | 94 | 84 | " | " |
| 199 | 88 | 93 | " | " |
| 200 | 95 | 96 | " | " |
| 201 | 100 | 100 | " | " |
| 202 | 86 | 87 | " | " |
| 203 | 87 | 89 | " | " |
| 204 | 100 | 100 | " | " |
| 205 | 100 | 100 | " | " |
| 206 | 100 | 98 | " | " |
| 207 | 98 | 99 | " | " |
| 208 | 94 | 88 | " | " |
| 209 | 100 | 83 | " | " |
| 210 | 86 | 100 | " | " |
| 211 | 99 | 94 | " | " |
| 212 | 94 | 98 | " | " |
| 213 | 93 | 86 | " | " |
| 214 | 100 | 86 | " | " |
| 215 | 98 | 96 | " | " |
| 216 | 96 | 100 | " | " |
| 217 | 94 | 97 | " | " |
| 218 | 100 | 100 | " | " |
| 219 | 92 | 98 | " | " |
| 220 | 100 | 99 | " | " |
| 221 | 87 | 86 | " | " |
| 222 | 86 | 89 | " | " |

TABLE 2-continued

| Compound No. | Leaf rust on wheat 50 | Powdery mildew on cucumber 50 | Phytotoxicity Wheat | Phytotoxicity Cucumber |
|---|---|---|---|---|
| 223 | 93 | 90 | " | " |
| 224 | 90 | 91 | " | " |
| 225 | 90 | 92 | " | " |
| 226 | 92 | 91 | " | " |
| 227 | 98 | 100 | " | " |
| 228 | 100 | 100 | " | " |
| 229 | 99 | 99 | " | " |
| 230 | 96 | 92 | " | " |
| 231 | 96 | 98 | " | " |
| 232 | 98 | 99 | " | " |
| 233 | 87 | 100 | " | " |
| 234 | 94 | 98 | " | " |
| 235 | 88 | 89 | " | " |
| 236 | 98 | 92 | " | " |
| 237 | 83 | 87 | " | " |
| 238 | 86 | 85 | " | " |
| 239 | 89 | 90 | " | " |
| 240 | 88 | 92 | " | " |
| 241 | 87 | 84 | " | " |
| 242 | 90 | 96 | " | " |
| 243 | 83 | 90 | " | " |
| 244 | 88 | 92 | " | " |
| 245 | 87 | 88 | " | " |
| 246 | 98 | 100 | " | " |
| 247 | 100 | 100 | " | " |
| 248 | 100 | 100 | " | " |
| 249 | 100 | 99 | " | " |
| 250 | 100 | 92 | " | " |
| 251 | 89 | 87 | " | " |
| 252 | 84 | 83 | " | " |
| 253 | 83 | 89 | " | " |
| 254 | 86 | 95 | " | " |
| 255 | 83 | 86 | " | " |
| 256 | 82 | 82 | " | " |
| 257 | 85 | 86 | " | " |
| 258 | 87 | 87 | " | " |
| 259 | 98 | 94 | " | " |
| 260 | 86 | 86 | " | " |
| 261 | 85 | 89 | " | " |
| 262 | 84 | 94 | " | " |
| 263 | 85 | 100 | " | " |
| 264 | 98 | 99 | " | " |
| 265 | 96 | 100 | " | " |
| 266 | 98 | 100 | " | " |
| 267 | 100 | 100 | " | " |
| 268 | 100 | 100 | " | " |
| 269 | 86 | 98 | " | " |
| 270 | 89 | 90 | " | " |
| 271 | 91 | 88 | " | " |
| 272 | 93 | 100 | " | " |
| 273 | 85 | 95 | " | " |
| 274 | 86 | 94 | " | " |
| 275 | 94 | 100 | " | " |
| 276 | 92 | 99 | " | " |
| 277 | 92 | 100 | " | " |
| 278 | 94 | 100 | " | " |
| 279 | 90 | 100 | " | " |
| 280 | 100 | 100 | " | " |
| 281 | 100 | 100 | " | " |
| 282 | 100 | 100 | " | " |
| 283 | 100 | 100 | " | " |
| 284 | 100 | 100 | " | " |
| 285 | 100 | 100 | " | " |
| 286 | 87 | 94 | " | " |
| 287 | 94 | 98 | " | " |
| 288 | 96 | 85 | " | " |
| 289 | 92 | 98 | " | " |
| 290 | 100 | 100 | " | " |
| 291 | 100 | 99 | " | " |
| 292 | 97 | 100 | " | " |
| 293 | 100 | 100 | " | " |
| 294 | 100 | 100 | " | " |
| 295 | 100 | 100 | " | " |
| 296 | 96 | 98 | " | " |
| 297 | 98 | 98 | " | " |
| 298 | 93 | 94 | " | " |
| 299 | 100 | 98 | " | " |
| 300 | 98 | 87 | " | " |
| 301 | 95 | 92 | " | " |
| 302 | 100 | 93 | " | " |
| 303 | 95 | 89 | " | " |
| 304 | 100 | 94 | " | " |
| 305 | 83 | 86 | " | " |
| 306 | 87 | 89 | " | " |
| 307 | 89 | 86 | " | " |
| 308 | 91 | 88 | " | " |
| 309 | 84 | 85 | " | " |
| 310 | 83 | 87 | " | " |
| 311 | 85 | 84 | " | " |
| 312 | 83 | 91 | " | " |
| 313 | 89 | 100 | " | " |
| 314 | 85 | 100 | " | " |
| 315 | 96 | 100 | " | " |
| 316 | 100 | 100 | " | " |
| 317 | 83 | 88 | " | " |
| 318 | 85 | 95 | " | " |
| 319 | 85 | 91 | " | " |
| 320 | 86 | 90 | " | " |
| 321 | 83 | 100 | " | " |
| 322 | 85 | 93 | " | " |
| 323 | 87 | 99 | " | " |
| 324 | 89 | 92 | " | " |
| 325 | 83 | 96 | " | " |
| 326 | 85 | 95 | " | " |
| 327 | 85 | 93 | " | " |
| 328 | 87 | 87 | " | " |
| 329 | 86 | 87 | " | " |
| 330 | 84 | 89 | " | " |
| 331 | 82 | 89 | " | " |
| 332 | 83 | 86 | " | " |
| 333 | 87 | 88 | " | " |
| 334 | 90 | 90 | " | " |
| Comparative compound A | 16 | 21 | " | " |
| Comparative compound B | 38 | 63 | " | " |
| Comparative compound C | 0 | 28 | " | " |
| Comparative compound D | 82 | — | " | — |
| Comparative compound E | — | 83 | — | 0 |

TABLE 2-continued

| Compound No. | Leaf rust on wheat 50 | Powdery mildew on cucumber 50 | Phytotoxicity Wheat | Phytotoxicity Cucumber |
|---|---|---|---|---|
| No treatment | 0 | 0 | — | — |

Notes:
Comparative compound A:

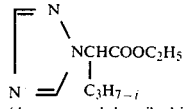

(A compound described in Japanese patent application unexamined prepublication "Kokai" Sho 52-27767)

Comparative compound B:

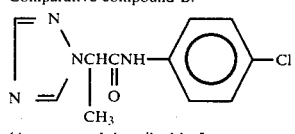

(A compound described in Japanese patent application unexamined prepublication "Kokai" Sho 52-27767)

Comparative compound C:

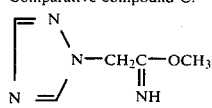

(A compound described in Japanese patent application unexamined prepublication "Kokai" Sho 52-27767)

Comparative compound D:
Ethylene-bis(dithiocarbamic acid) manganese salt (known under the tradename "Manneb")

Comparative compound E:
Dithiocarbonic acid S,S—6-methylquinoxaline-2,3-di-yl ester (known under the tradename "Quinomethionate")

EXAMPLE 22

This Example illustrates tests of controlling leaf rust in wheat in preventative treatment when the test compound is applied at low concentrations.

The effects of the test compounds against leaf rust disease in wheat were estimated in the same manner as in Example 20, while the test compounds were applied at low concentrations as indicated in Tables 3 and 4 below. The tests were conducted with three replicates. The test results (expressed as averaged % Control) are given in Tables 3 and 4.

TABLE 3

| Compound No. | 25 | 12.5 | 6.25 |
|---|---|---|---|
| 6 | 99 | 92 | 88 |
| 12 | 95 | 97 | 98 |
| 20 | 98 | 94 | 90 |
| 38 | 100 | 95 | 90 |
| 39 | 93 | 91 | 86 |
| 40 | 90 | 89 | 82 |
| 46 | 98 | 92 | 89 |
| 83 | 92 | 90 | 87 |
| 106 | 92 | 87 | 84 |
| 111 | 87 | 78 | 73 |
| 112 | 84 | 80 | 70 |
| 121 | 98 | 91 | 81 |
| 123 | 98 | 100 | 100 |
| 124 | 95 | 92 | 90 |
| 127 | 96 | 98 | 98 |
| 129 | 95 | 91 | 82 |
| 130 | 96 | 94 | 83 |
| 132 | 96 | 92 | 95 |
| 135 | 92 | 87 | 78 |
| 141 | 100 | 99 | 97 |

TABLE 3-continued

| Compound No. | 25 | 12.5 | 6.25 |
|---|---|---|---|
| 142 | 100 | 99 | 100 |
| 143 | 99 | 94 | 90 |
| 145 | 99 | 90 | 71 |
| 146 | 94 | 87 | 73 |
| 147 | 96 | 89 | 78 |
| 151 | 92 | 84 | 71 |
| 152 | 100 | 83 | 68 |
| 153 | 100 | 92 | 67 |
| 155 | 91 | 82 | 70 |
| 171 | 91 | 86 | 81 |
| 177 | 98 | 100 | 100 |
| 182 | 95 | 96 | 93 |
| 183 | 96 | 98 | 100 |
| 185 | 97 | 94 | 89 |
| 190 | 98 | 99 | 97 |
| 191 | 97 | 93 | 89 |
| 192 | 97 | 98 | 99 |
| 197 | 92 | 87 | 73 |
| 201 | 96 | 95 | 98 |
| 204 | 97 | 99 | 100 |
| 205 | 96 | 98 | 95 |
| 206 | 96 | 97 | 99 |
| 211 | 96 | 92 | 90 |
| 214 | 94 | 92 | 86 |
| 215 | 93 | 93 | 85 |
| 218 | 91 | 83 | 69 |
| 220 | 94 | 90 | 81 |
| 236 | 92 | 87 | 68 |
| 247 | 99 | 91 | 84 |
| 248 | 98 | 94 | 87 |
| 249 | 100 | 90 | 77 |
| 250 | 97 | 84 | 80 |
| 267 | 95 | 98 | 99 |
| 268 | 97 | 94 | 84 |
| 280 | 97 | 99 | 99 |
| 281 | 99 | 98 | 96 |
| 283 | 95 | 85 | 67 |
| 284 | 100 | 92 | 87 |
| 285 | 98 | 95 | 90 |
| 290 | 98 | 91 | 79 |
| 291 | 95 | 92 | 81 |
| 293 | 100 | 99 | 100 |
| 294 | 96 | 93 | 90 |
| 295 | 100 | 90 | 87 |
| 299 | 95 | 90 | 84 |
| 302 | 91 | 83 | 76 |
| 304 | 94 | 90 | 81 |
| 316 | 97 | 97 | 95 |
| Comparative compound A | 7 | 0 | 0 |
| Comparative compound B | 12 | 5 | 0 |
| Comparative compound C | 0 | 0 | 0 |
| Comparative compound D | 65 | 46 | 18 |

TABLE 4

| Compound No. | 3.13 | 1.56 | 0.78 |
|---|---|---|---|
| 12 | 94 | 96 | 87 |
| 38 | 85 | 82 | 75 |
| 121 | 80 | 73 | 68 |
| 123 | 98 | 89 | 89 |
| 124 | 85 | 82 | 76 |
| 127 | 95 | 95 | 87 |
| 141 | 87 | 86 | 78 |
| 142 | 98 | 97 | 81 |
| 177 | 98 | 97 | 89 |
| 183 | 97 | 95 | 87 |
| 190 | 98 | 92 | 79 |
| 192 | 95 | 94 | 83 |
| 201 | 95 | 92 | 82 |

TABLE 4-continued

| Compound No. | Control (%) Concentration of active ingredient compound sprayed (ppm) | | |
|---|---|---|---|
| | 3.13 | 1.56 | 0.78 |
| 204 | 98 | 96 | 95 |
| 205 | 94 | 90 | 87 |
| 206 | 93 | 87 | 79 |
| 267 | 97 | 90 | 81 |
| 280 | 98 | 95 | 94 |
| 281 | 96 | 90 | 89 |
| 293 | 94 | 85 | 80 |
| 316 | 92 | 86 | 81 |
| Comparative compound A | 0 | 0 | 0 |
| Comparative compound B | 0 | 0 | 0 |
| Comparative compound C | 0 | 0 | 0 |
| Comparative compound D | 7 | 0 | 0 |

EXAMPLE 23

This Example illustrates tests of controlling leaf rust in wheat in curative treatment.

The procedures of Example 20 for controlling the wheat leaf rust disease were repeated but except that the spraying of the composition under test was made one day after the inoculation of the wheat leaf rust fungi. The test results obtained are set out in Table 5 below.

TABLE 5

| Compound No. | Concentration of test compound sprayed (ppm) | Control (%) | Phytotoxicity |
|---|---|---|---|
| 4 | 50 | 92 | 0 |
| 6 | " | 100 | " |
| 12 | " | 100 | " |
| 19 | " | 98 | " |
| 20 | " | 100 | " |
| 38 | " | 100 | " |
| 39 | " | 99 | " |
| 46 | " | 98 | " |
| 83 | " | 98 | " |
| 106 | " | 98 | " |
| 111 | " | 100 | " |
| 112 | " | 95 | " |
| 121 | " | 100 | " |
| 123 | " | 100 | " |
| 124 | " | 98 | " |
| 125 | " | 91 | " |
| 127 | " | 100 | " |
| 129 | " | 94 | " |
| 132 | " | 93 | " |
| 135 | " | 93 | " |
| 141 | " | 100 | " |
| 142 | " | 100 | " |
| 143 | " | 100 | " |
| 145 | " | 100 | " |
| 146 | " | 100 | " |
| 147 | " | 97 | " |
| 152 | " | 100 | " |
| 153 | " | 100 | " |
| 155 | " | 100 | " |
| 171 | " | 99 | " |
| 175 | " | 92 | " |
| 177 | " | 100 | " |
| 182 | " | 94 | " |
| 183 | " | 100 | " |
| 185 | " | 100 | " |
| 190 | " | 100 | " |
| 191 | " | 99 | " |
| 192 | " | 100 | " |
| 201 | " | 100 | " |
| 204 | " | 100 | " |
| 205 | " | 100 | " |
| 206 | " | 100 | " |
| 214 | " | 96 | " |
| 228 | " | 97 | " |
| 236 | " | 95 | " |
| 247 | " | 100 | " |
| 248 | " | 94 | " |
| 249 | " | 100 | " |
| 250 | " | 95 | " |
| 267 | " | 100 | " |
| 268 | " | 97 | " |
| 279 | " | 92 | " |
| 280 | " | 100 | " |
| 281 | " | 100 | " |
| 283 | " | 92 | " |
| 284 | " | 100 | " |
| 285 | " | 100 | " |
| 290 | " | 94 | " |
| 291 | " | 92 | " |
| 292 | " | 93 | " |
| 293 | " | 95 | " |
| 294 | " | 98 | " |
| 295 | " | 100 | " |
| 299 | " | 92 | " |
| 304 | " | 99 | " |
| 316 | " | 98 | " |
| Comparative compound A | " | 10 | " |
| Comparative compound B | " | 23 | " |
| Comparative compound C | " | 0 | " |
| Comparative compound D | " | 36 | " |
| No treatment | — | 0 | — |

EXAMPLE 24

This Example illustrates tests of controlling powdery mildew in cucumber when the test compound was applied at low concentrations.

The effects of the test compounds for controlling the powdery mildew disease in cucumber were estimated in the same manner as in Example 21, while the test compounds were applied at low concentrations as indicated in Table 6 below. The test results obtained (expressed as averaged % Control) are tabulated in Table 6 below.

TABLE 6

| Compound No. | Control (%) Concentration of test compound sprayed (ppm) | | |
|---|---|---|---|
| | 20 | 5 | 1.25 |
| 3 | 100 | 70 | 66 |
| 17 | 96 | 81 | 62 |
| 19 | 98 | 82 | 76 |
| 23 | 100 | 100 | 83 |
| 83 | 95 | 84 | 63 |
| 93 | 100 | 98 | 83 |
| 106 | 100 | 92 | 74 |
| 108 | 100 | 99 | 64 |
| 113 | 100 | 81 | 66 |
| 121 | 100 | 100 | 94 |
| 123 | 100 | 95 | 91 |
| 124 | 100 | 94 | 84 |
| 125 | 100 | 99 | 78 |
| 129 | 100 | 100 | 100 |
| 130 | 100 | 99 | 96 |
| 132 | 100 | 100 | 100 |
| 141 | 100 | 95 | 80 |
| 142 | 100 | 100 | 87 |
| 152 | 100 | 100 | 62 |
| 154 | 100 | 83 | 68 |
| 155 | 100 | 92 | 73 |
| 168 | 90 | 74 | 61 |
| 177 | 100 | 100 | 89 |
| 188 | 100 | 97 | 93 |

TABLE 6-continued

| Compound No. | Control (%) Concentration of test compound sprayed (ppm) | | |
|---|---|---|---|
| | 20 | 5 | 1.25 |
| 189 | 100 | 67 | 61 |
| 192 | 100 | 85 | 85 |
| 204 | 98 | 81 | 73 |
| 205 | 95 | 79 | 75 |
| 210 | 100 | 97 | 91 |
| 216 | 100 | 81 | 74 |
| 218 | 100 | 92 | 84 |
| 220 | 94 | 83 | 70 |
| 227 | 100 | 92 | 81 |
| 228 | 100 | 92 | 67 |
| 229 | 98 | 73 | 67 |
| 233 | 100 | 99 | 75 |
| 247 | 100 | 100 | 100 |
| 248 | 100 | 94 | 89 |
| 263 | 91 | 79 | 62 |
| 265 | 100 | 96 | 82 |
| 266 | 99 | 98 | 85 |
| 267 | 100 | 98 | 79 |
| 272 | 96 | 84 | 73 |
| 279 | 100 | 100 | 97 |
| 280 | 100 | 100 | 100 |
| 281 | 100 | 100 | 97 |
| 282 | 100 | 98 | 92 |
| 283 | 100 | 100 | 89 |
| 284 | 100 | 100 | 98 |
| 285 | 100 | 100 | 100 |
| 292 | 100 | 100 | 86 |
| 293 | 100 | 100 | 97 |
| 294 | 100 | 90 | 82 |
| 295 | 99 | 97 | 89 |
| 315 | 100 | 88 | 92 |
| 316 | 100 | 100 | 95 |
| 321 | 100 | 99 | 68 |
| Comparative compound A | 15 | 0 | 0 |
| Comparative compound B | 38 | 16 | 0 |
| Comparative compound C | 18 | 0 | 0 |
| Comparative compound E | 63 | 21 | 0 |

EXAMPLE 25

This Example illustrates tests of controlling brown spot in rice.

Rice plants (variety: Asahi) were grown in soil in 9 cm-diameter porous pots in a greenhouse. At the four true-leaf stage, the rice plants were sprayed with the composition under test which was prepared by diluting the wettable powder of Example 14 with water to a concentration of the active compound as indicated in Table 7 below. One day after the treatment, the treated rice plants were inoculated with a suspension of conidiospores of rice brown spot fungi (*Cochliobolus miyabeanus*). 5 Days after inoculation, the number of the lesions on the fourth leaf developed by infection was counted. The degree of control (%) was then evaluated according to the under-mentioned equation. Degree of phytotoxicity of the test compound was also estimated by the same grading as in Example 20. The test results are set out in Table 7 below.

$$\text{Control (\%)} = \left\{ 1 - \frac{\text{Number of lesions developed by infection in a treated leaf}}{\text{Number of lesions developed by infection in a non-treated leaf}} \right\} \times 100$$

TABLE 7

| Compound No. | Concentration of test compound sprayed (ppm) | Control (%) | Phyto-toxicity |
|---|---|---|---|
| 1 | 100 | 92 | 0 |
| 3 | " | 95 | " |
| 4 | " | 100 | " |
| 5 | " | 100 | " |
| 6 | " | 100 | " |
| 11 | " | 100 | " |
| 12 | " | 100 | " |
| 17 | " | 93 | " |
| 19 | " | 100 | " |
| 20 | " | 100 | " |
| 24 | " | 87 | " |
| 25 | " | 89 | " |
| 30 | " | 94 | " |
| 32 | " | 93 | " |
| 38 | " | 100 | " |
| 39 | " | 100 | " |
| 41 | " | 100 | " |
| 42 | " | 100 | " |
| 45 | " | 89 | " |
| 55 | " | 98 | " |
| 58 | " | 98 | " |
| 63 | " | 94 | " |
| 72 | " | 94 | " |
| 76 | " | 92 | " |
| 77 | " | 90 | " |
| 83 | " | 89 | " |
| 89 | " | 88 | " |
| 94 | " | 84 | " |
| 96 | " | 86 | " |
| 105 | " | 99 | " |
| 106 | " | 100 | " |
| 107 | " | 92 | " |
| 108 | " | 91 | " |
| 109 | " | 90 | " |
| 111 | " | 100 | " |
| 112 | " | 100 | " |
| 121 | " | 100 | " |
| 123 | " | 100 | " |
| 124 | " | 97 | " |
| 125 | " | 100 | " |
| 127 | " | 100 | " |
| 135 | " | 85 | " |
| 139 | " | 95 | " |
| 141 | " | 86 | " |
| 152 | " | 95 | " |
| 158 | " | 98 | " |
| 160 | " | 97 | " |
| 161 | " | 95 | " |
| 166 | " | 84 | " |
| 170 | " | 92 | " |
| 171 | " | 98 | " |
| 174 | " | 92 | " |
| 180 | " | 90 | " |
| 182 | " | 89 | " |
| 183 | " | 86 | " |
| 187 | " | 88 | " |
| 188 | " | 98 | " |
| 190 | " | 82 | " |
| 192 | " | 96 | " |
| 195 | " | 87 | " |
| 196 | " | 90 | " |
| 197 | " | 95 | " |
| 200 | " | 82 | " |
| 201 | " | 100 | " |
| 204 | " | 100 | " |
| 205 | " | 100 | " |
| 206 | " | 100 | " |
| 207 | " | 100 | " |
| 208 | " | 100 | " |

TABLE 7-continued

| Compound No. | Concentration of test compound sprayed (ppm) | Control (%) | Phytotoxicity |
|---|---|---|---|
| 214 | " | 87 | " |
| 218 | " | 86 | " |
| 222 | " | 86 | " |
| 227 | " | 96 | " |
| 228 | " | 97 | " |
| 229 | " | 92 | " |
| 230 | " | 98 | " |
| 231 | " | 94 | " |
| 236 | " | 94 | " |
| 241 | " | 89 | " |
| 242 | " | 94 | " |
| 246 | " | 96 | " |
| 247 | " | 98 | " |
| 248 | " | 98 | " |
| 249 | " | 96 | " |
| 253 | " | 99 | " |
| 267 | " | 90 | " |
| 279 | " | 94 | " |
| 280 | " | 89 | " |
| 281 | " | 86 | " |
| 282 | " | 98 | " |
| 283 | " | 89 | " |
| 302 | " | 85 | " |
| 303 | " | 99 | " |
| 304 | " | 100 | " |
| 310 | " | 98 | " |
| 319 | " | 98 | " |
| 321 | " | 100 | " |
| 325 | " | 87 | " |
| 329 | " | 87 | " |
| 330 | " | 85 | " |
| Comparative compound A | " | 0 | " |
| Comparative compound B | " | 8 | " |
| Comparative compound C | " | 0 | " |
| Comparative compound F | " | 82 | " |
| No treatment | — | 0 | — |

Note:
Comparative compound F: 2,4-Dichloro-6-(O-chloroanilino)-1,3,5-triazine (known as Triazine).

EXAMPLE 26

This Example illustrates tests of controlling brown spot in rice when the test compound is applied at low concentrations.

The effects of the test compounds against brown spot disease in rice were estimated in the same manner as in Example 25, while the test compounds were applied at low concentrations as indicated in Table 8. The tests were conducted with three replicates. The test results (expressed as averaged % Control) are shown in Table 8.

TABLE 8

| Compound No. | Control (%) Concentration of active ingredient compound sprayed (ppm) | | |
|---|---|---|---|
| | 50 | 25 | 12.5 |
| 4 | 96 | 90 | 78 |
| 6 | 97 | 81 | 70 |
| 12 | 98 | 83 | 68 |
| 19 | 99 | 80 | 69 |
| 20 | 98 | 91 | 84 |
| 38 | 98 | 98 | 92 |
| 39 | 99 | 96 | 91 |
| 41 | 97 | 85 | 82 |
| 42 | 95 | 82 | 79 |
| 55 | 90 | 74 | 64 |
| 58 | 94 | 81 | 73 |
| 63 | 88 | 76 | 68 |
| 72 | 89 | 84 | 68 |
| 105 | 94 | 83 | 69 |
| 111 | 100 | 95 | 86 |
| 112 | 99 | 92 | 77 |
| 121 | 97 | 82 | 70 |
| 123 | 87 | 80 | 73 |
| 124 | 94 | 82 | 65 |
| 125 | 94 | 88 | 79 |
| 127 | 93 | 89 | 82 |
| 158 | 97 | 84 | 71 |
| 171 | 96 | 92 | 74 |
| 201 | 97 | 82 | 72 |
| 204 | 100 | 97 | 91 |
| 205 | 100 | 92 | 85 |
| 206 | 99 | 90 | 81 |
| 207 | 100 | 90 | 76 |
| 208 | 100 | 89 | 79 |
| 230 | 94 | 87 | 63 |
| 304 | 97 | 89 | 69 |
| 321 | 100 | 74 | 62 |
| Comparative compound A | 0 | 0 | 0 |
| Comparative compound B | 0 | 0 | 0 |
| Comparative compound C | 0 | 0 | 0 |
| Comparative compound F | 76 | 61 | 23 |

EXAMPLE 27

This Example sets out the tests of estimating the activities of the test compounds against various kinds of plant-pathogenic fungi.

A compound of this invention was dissolved in acetone, and 1 ml of the resultant solution was admixed with 20 ml of PSA medium (pH 5.8) at 60° C. in a Petri dish of 9 cm diameter to prepare an agar plate containing the test compound at a predetermined concentration as indicated in Table 9 below. The Petri dish, without the upper cover, was allowed to stand overnight to evaporate acetone off, and the agar plate so prepared was inoculated with a loopful amount of a suspension of spores of the test microorganism which were previously incubated on PSA slant medium. After incubation for 48 hours at 24° C., the degrees of the growth of the test microorganisms were assessed by the following grading. The results are listed in Table 9 below.

Grades of growth of the fungi:

—: No growth at all.

⊥: Formation of a few colonies was observed in the inoculated region of the agar plate where the spore suspension had been applied, and the growth was greatly suppressed.

+: Formation of many colonies was observed in the inoculated region of the agar plate where the spore suspension had been applied, but the growth was so suppressed not to cover the whole surface of said region.

++: Growth covered the whole surface of the inoculated region of the agar plate where the spore suspension had been applied, but the growth was still poor.

+++: Growth covered the whole surface of the inoculated region of the agar plate where the spore suspension had been applied, and the growth was good.

termined concentration of the active compound indicated in Table 10 below. One day after the treatment,

TABLE 9

| Compound No. | Concentration of test compound (ppm) | Tested and degrees of the fungal growth | | | | | | | | | |
|---|---|---|---|---|---|---|---|---|---|---|---|
| | | A | B | C | D | E | F | G | H | I | J |
| 2 | 10 | − | ± | ± | − | ++ | − | − | ± | − | − |
| 6 | " | − | − | − | − | + | − | − | ± | − | − |
| 17 | " | − | ± | ± | ± | ++ | − | − | ± | ± | − |
| 20 | " | − | − | − | − | ++ | − | − | − | − | − |
| 23 | " | − | − | − | − | + | − | − | − | − | − |
| 38 | " | − | − | − | − | + | − | − | − | − | − |
| 39 | " | − | − | − | − | ± | − | − | − | − | − |
| 42 | " | − | − | ± | − | + | − | − | − | − | − |
| 55 | " | − | ± | ± | − | ++ | − | − | ± | ± | − |
| 72 | " | − | − | − | − | + | − | − | − | − | − |
| 80 | " | − | ± | + | − | ++ | − | − | ± | − | ± |
| 89 | " | − | ± | ± | + | ++ | − | ± | ± | ± | − |
| 93 | " | − | ± | ± | ± | ++ | − | − | − | − | − |
| 107 | " | − | ± | ± | + | ++ | − | − | ± | − | ± |
| 111 | " | − | ± | ± | ± | ± | − | ± | ± | ± | − |
| 112 | " | − | ± | ± | ± | + | − | ± | ± | ± | − |
| 118 | " | − | ± | − | ± | ++ | − | ± | − | − | − |
| 119 | " | − | ± | − | + | ++ | − | ± | − | − | − |
| 123 | " | − | − | − | − | + | − | − | − | − | − |
| 125 | " | − | − | ± | − | + | − | − | − | − | − |
| 127 | " | − | − | − | − | + | − | − | − | − | − |
| 129 | " | − | − | ± | ± | ++ | − | − | ± | ± | ± |
| 136 | " | ± | ± | + | + | ++ | − | + | ± | ± | ± |
| 142 | " | − | − | + | − | + | − | − | − | − | − |
| 170 | " | − | − | + | − | + | − | − | − | − | − |
| 171 | " | − | − | − | − | ± | − | − | − | − | − |
| 177 | " | − | − | ± | − | + | − | − | − | − | − |
| 183 | " | − | ± | ± | − | + | − | − | − | ± | ± |
| 192 | " | − | − | ± | − | + | − | − | − | − | − |
| 196 | " | − | ± | ± | ± | ++ | − | − | ± | ± | ± |
| 203 | " | − | ± | − | − | + | − | − | − | ± | − |
| 204 | " | − | − | − | − | ± | − | − | − | − | − |
| 205 | " | − | − | − | − | + | − | − | − | − | − |
| 206 | " | − | − | − | − | + | − | − | − | − | − |
| 228 | " | − | − | − | − | + | − | − | − | − | − |
| 242 | " | − | ± | ± | ± | ++ | − | − | ± | ± | ± |
| 247 | " | − | − | ± | − | + | − | − | − | − | − |
| 248 | " | − | − | + | − | + | − | − | ± | − | − |
| 267 | " | − | − | ± | − | + | − | − | − | ± | − |
| 271 | " | − | + | + | + | ++ | − | ± | ± | ± | ± |
| 272 | " | − | ± | ± | − | ++ | − | − | ± | ± | ± |
| 279 | " | − | + | + | − | + | − | − | ± | − | ± |
| 280 | " | − | + | + | − | + | − | − | − | ± | − |
| 284 | " | − | ± | + | − | + | − | − | − | − | ± |
| 285 | " | − | + | + | + | ++ | − | ± | + | + | + |
| 292 | " | − | + | ± | ± | ++ | − | ± | ± | ± | ± |
| 294 | " | − | + | ± | ± | ++ | − | ± | + | ± | ± |
| 303 | " | − | − | − | − | ± | − | − | − | − | − |
| 304 | " | − | − | − | − | ± | − | − | − | − | − |
| 305 | " | − | − | − | ± | + | − | − | − | − | − |
| 307 | " | ± | + | + | + | ++ | − | + | ± | ± | + |
| 316 | " | − | ± | ± | ± | ++ | − | − | ± | ± | ± |
| No addition | | +++ | +++ | +++ | +++ | +++ | +++ | +++ | +++ | +++ | +++ |

Note:
A — *Cladosporium fulvum* in tomato.
B — *Gibberella fujikuroi* in rice.
C — *Glomerella cingulate* in vine.
D — *Alternaria kikuchiana* in pear.
E — *Valsa mali* in apple.
F — *Piricularia oryzae* in rice.
G — *Cochliobolus miyabeanus* in rice.
H — *Cercospora beticola* in beet.
I — *Colletotrichum lagenarium* in cucumber.
J — *Fusarium oxysporum* in cucumber.

EXAMPLE 28

This Example illustrates tests of controlling gummy stem blight in cucumber.

Cucumber plants (variety: Sagami-Hanjiro) were grown in soil in 9 cm-diameter porous pots in a greenhouse. At the first true-leaf stage, the cucumber seedlings were sprayed with 10 ml per pot of the composition under test which was prepared by diluting the wettable powder of Example 14 with water to a predetermined concentration of the active compound indicated in Table 10 below. One day after the treatment, the treated leaves of the cucumber plants were inoculated by placing on the surface of the treated leaves a fragment of PSA medium containing the gummy stem blight fungus (*Mycoshaerella melonis*) as inoculum. This fragment of the PSA medium as the inoculum had been prepared by incubating the fungus on the surface of PSA medium at 24° C. for 4 days and then piercing the ends of the colony with a corkborer of 8 mm in diameter. The inoculated cucumber plants were then confined in a humid room at 24° C. for 3 days to promote the development of lesions of the infection. The degree of infection was estimated by measuring the length of lesions on the infected leaves and evaluating the degree of control (%) according to the under-mentioned equation. The degree of phytotoxicity of the test compound to cucumber plant was estimated by the same grading as in Example 20.

The tests were conducted with three replicates. The test results are given in Table 10 below.

$$\text{Control (\%)} = \left(1 - \frac{\text{Averaged length of lesions in treated plot}}{\text{Averaged length of lesions in non-treated plot}}\right) \times 100$$

TABLE 10

| Compound No. | Concentration of active ingredient compound sprayed (ppm) | Control (%) | Phytotoxicity |
|---|---|---|---|
| 6 | 200 | 97 | 0 |
| 39 | " | 94 | " |
| 83 | " | 90 | " |
| 106 | " | 88 | " |
| 111 | " | 89 | " |
| 123 | " | 100 | " |
| 127 | " | 98 | " |
| 131 | " | 98 | " |
| 141 | " | 96 | " |
| 177 | " | 94 | " |
| 183 | " | 97 | " |
| 192 | " | 96 | " |
| 204 | " | 100 | " |
| 220 | " | 93 | " |
| 250 | " | 90 | " |
| 267 | " | 95 | " |
| 280 | " | 99 | " |
| 284 | " | 96 | " |
| 304 | " | 90 | " |
| 316 | " | 92 | " |
| Comparative compound A | " | 0 | " |
| Comparative compound B | " | 12 | " |
| Comparative compound C | " | 0 | " |
| Comparative compound G | " | 62 | " |

Comparative compound G: Methyl 1-(butylcarbamoyl)-2-benzimidazol carbamate (known as Benomil)

EXAMPLE 29

This Example illustrates tests of controlling Fusarium wilt in cucumber.

In a field of cucumber plants in a greenhouse where the Fusarium wilt had been prevailing, the soil surface of the field was admixed well with 100 g/m² of an inoculum of Fusarium wilt fungi (*Fusarium oxysporum* f. sp. *cucumerinum*) which was incubated in a mixture of soil and wheat bran, for the purpose of promoting the development of the disease. 3 Days after the inoculation, the surface of the soil was treated by drenching thereon 3 l/m² of the composition under test which had been prepared by diluting the wettable powder of Example 14 with water to a particular concentration of the active compound as indicated in Table 11 below. One day after the drenching of the composition under test, seeds of cucumber (variety: Sagami-Hamjiro) were sown at a rate of 100 pieces of seed per plot and then allowed to germinate and grow. 30 Days later, the number of the damping-off cucumber plants by the fungal infection was counted and the percentage of damping-off cucumber plants was calculated on the basis of the number of the seed sown per plot. The degree of control (%) was evaluated according to the undermentioned equation. The degree of phytotoxicity was also estimated by the same grading as in Example 20.

The tests were conducted with three replicates, using test plots each of an area of 0.5 m² for a particular concentration of one test compound. The test results obtained are shown in Table 11 below.

$$\text{Control (\%)} = \left(1 - \frac{\text{Average (\%) of damping-off plants in treated plot}}{\text{Average (\%) of damping-off plants in non-treated plot}}\right) \times 100$$

TABLE 11

| Compound No. | Rate of application of active ingredient compound (kg per 10 ares) | Control (%) | Phyto-toxicity |
|---|---|---|---|
| 123 | 1.0 kg | 96 | 0 |
| " | 0.5 kg | 80 | 0 |
| " | 0.25 kg | 70 | 0 |
| 131 | 1.0 kg | 100 | 0 |
| " | 0.5 kg | 95 | 0 |
| " | 0.25 kg | 80 | 0 |
| 204 | 1.0 kg | 98 | 0 |
| " | 0.5 kg | 83 | 0 |
| " | 0.25 kg | 75 | 0 |
| Comparative compound A | 1.0 kg | 12 | 0 |
| Comparative compound A | 0.5 kg | 5 | 0 |
| Comparative compound A | 0.25 kg | 0 | 0 |
| Comparative compound B | 1.0 kg | 9 | 0 |
| Comparative compound B | 0.5 kg | 3 | 0 |
| Comparative compound B | 0.25 kg | 0 | 0 |
| Comparative compound C | 1.0 kg | 5 | 0 |
| Comparative compound C | 0.5 kg | 0 | 0 |
| Comparative compound C | 0.25 kg | 0 | 0 |
| Chloropicrin (comparative)* | 30 l | 68 | 0 |

*The comparative treatment with chloropicrin was conducted according to the habitual treatment. Thus, 2 ml of chloropicrin per 30 cm² of the field was shanked into the soil to 15 cm deep and the soil surface was immediately covered with a sheet of polyvinyl chloride. 10 Days later, the sheet was taken off and the soil surface was plowed in 15 cm deep to remove the chloropicrin gas. 7 Days later, seeds of cucumber were sown.

What we claim is:

1. A 1,2,4-triazole derivative of the general formula

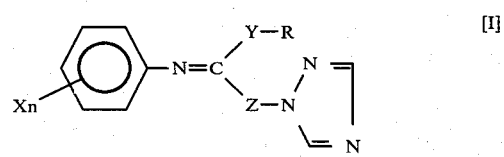

wherein X may be the same or different and denotes a halogen atom, a ($C_1$–$C_4$)alkyl group, a ($C_1$–$C_4$)alkoxyl group, a ($C_1$–$C_4$)alkylthio group, a ($C_1$–$C_4$)alkylsulfinyl group, a ($C_1$–$C_4$)alkylsulfonyl group, a trifluoromethyl group, a nitro group or a cyano group;

n is an integer of 0 to 5;

R denotes a $(C_1-C_4)$alkyl group, a $(C_2-C_4)$alkenyl group, a $(C_2-C_4)$alkynyl group, a $(C_1-C_4)$alkoxy-$(C_1-C_4)$alkyl group, a $(C_1-C_4)$alkylthio-$(C_1-C_4)$alkyl group, a $(C_3-C_6)$cycloalkyl group, a $(C_3-C_6)$cycloalkyl-$(C_1-C_4)$alkyl group, a phenyl group, a mono-halophenyl group, a di-halophenyl group, a tri-halophenyl group, or a phenyl$(C_1-C_4)$alkyl group of which the phenyl may optionally bear up to three substituents selected from a halogen atom, a $(C_1-C_4)$alkyl group, a $(C_1-C_4)$alkoxyl group, a $(C_1-C_4)$alkylthio group, a $(C_1-C_4)$alkylsulfonyl group, trifluoromethyl group, cyano group and nitro group, these substituents being the same or different from each other;

Y denotes an oxygen atom or a sulfur atom; and

Z denotes a linear or branched $(C_1-C_6)$alkylene group, and a salt of said 1,2,4-triazole derivative.

2. A 1,2,4-triazole derivative of claim 1 which is of the general formula

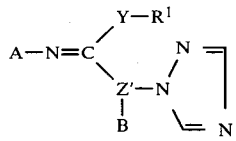   [Ia]

wherein A denotes a phenyl group, a chlorophenyl group, a bromophenyl group, a fluorophenyl group, an iodophenyl group, a cyanophenyl group, a nitrophenyl group, a trifluoromethylphenyl group, a dichlorophenyl group, a dibromophenyl group, a difluorophenyl group, a bromochlorophenyl group, a chlorofluorophenyl group, a chloroiodophenyl group, a trifluoromethylchlorophenyl group, a trichlorophenyl group, a dichlorofluorophenyl group, a methylchlorophenyl group, a methylnitrophenyl group, a methylcyanophenyl group, a trifluoromethyl-methylphenyl group, a trifluoromethyl-dichlorophenyl group, a methoxychlorophenyl group, a methoxydichlorophenyl group, a $(C_1-C_4)$alkylphenyl group, a di-$(C_1-C_4)$alkylphenyl group, a $(C_1-C_4)$alkoxyphenyl group, a $(C_1-C_4)$alkylthiophenyl group, a $(C_1-C_4)$alkylsulfinylphenyl group, a $(C_1-C_4)$alkylsulfonylphenyl group or a $(C_1-C_4)$alkylsulfonyl-bromophenyl group;

$R^1$ denotes a $(C_1-C_4)$alkyl group, a $(C_2-C_4)$alkenyl group, a $(C_1-C_4)$alkoxy-$(C_1-C_4)$alkyl group, a methylthio$(C_1-C_4)$alkyl group, a cyclohexyl group, a cyclopentyl group, a cyclopentyl-$(C_1-C_4)$alkyl group, a benzyl group, a chlorobenzyl group, a fluorobenzyl group, an iodobenzyl group, a cyanobenzyl group, a nitrobenzyl group, a dichlorobenzyl group, a trichlorobenzyl group, a chlorobromobenzyl group, a chlorofluorobenzyl group, a chlorocyanobenzyl group, a chloro-trifluoromethylbenzyl group, a mono- or di-$(C_1-C_4)$alkylbenzyl group, a $(C_1-C_4)$alkoxybenzyl group, a $(C_1-C_4)$alkyl-chlorobenzyl group, a $(C_1-C_4)$alkyl-nitrobenzyl group, a $(C_1-C_4)$alkylthiobenzyl group, a methylsulfonylbenzyl group, a methylsulfonylchlorobenzyl group, an ethylsulfinylbenzyl group, a phenylethyl group, a methyldichlorophenylethyl group, a 1-phenyl-propyl group, a 1-chlorophenylpropyl group, a phenyl group, a chlorophenyl group, a dichlorophenyl group, a dichlorofluorophenyl group, or a $(C_2-C_4)$alkynyl group;

Y is an oxygen atom or a sulfur atom;

$Z'$ is a linear $(C_1-C_3)$alkylene group; and

B is a hydrogen atom or a $(C_1-C_4)$alkyl group, and a salt of said 1,2,4-triazole derivative.

3. The compound of claim 2 in which A is a chlorophenyl group, a fluorophenyl group, a trifluoromethylphenyl group, a dichlorophenyl group, a chlorofluorophenyl group or a trifluoromethyl-chlorophenyl group.

4. The compound of claim 2 in which $R^1$ is a benzyl group, a monochlorobenzyl group or a dichlorobenzyl group.

5. The compound of claim 2 in which $Z'$ is a methylene group ($-CH_2-$) when B is the hydrogen atom.

6. The compound of claim 2 in which $Z'$ is a methine group when B is a methyl group.

7. The compound of claim 2 in which Y is the sulfur atom; A is a chlorophenyl group, a fluorophenyl group, a trifluoromethylphenyl group, a dichlorophenyl group, a chlorofluorophenyl group or a trifluoromethyl-chlorophenyl group; $R^1$ is a benzyl group, a monochlorobenzyl group or a dichlorobenzyl group; $Z'$ is a methylene group when B is the hydrogen atom, or $Z'$ is a methine group when B is the methyl group.

8. A 1,2,4-triazole derivative of claim 2 which is of the general formula

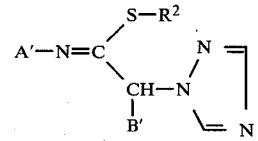   [Ib]

wherein $A'$ denotes a 2,4-dichlorophenyl group, a 2-chloro-4-fluorophenyl group, or a 2-trifluoromethyl-4-chlorophenyl group;

$R^2$ denotes a benzyl group, a 4-chlorobenzyl group, a 2,4-dichlorobenzyl group or a 3,4-dichlorobenzyl group, and $B'$ denotes a hydrogen atom or a methyl group, and a salt of said 1,2,4-triazole derivative.

9. A 1,2,4-triazole derivative of claim 2 which is of the general formula

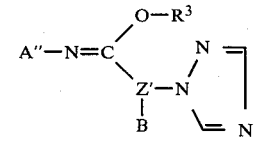   [Ic]

wherein $A''$ denotes a phenyl group, a chlorophenyl group, a bromophenyl group, a fluorophenyl group, an iodophenyl group, a cyanophenyl group, a nitrophenyl group, a trifluoromethylphenyl group, a dichlorophenyl group, a difluorophenyl group, a bromochlorophenyl group, a chlorofluorophenyl group, a chloroiodophenyl group, a trifluoromethylchlorophenyl group, a trichlorophenyl group, a dichlorofluorophenyl group, a methylchlorophenyl group, a methylnitrophenyl group, a methylcyanophenyl group, a trifluoromethyl-dichlorophenyl group, a methoxychlorophenyl group, a methoxy-dichlorophenyl group, a $(C_1-C_4)$alkylphenyl group a di-$(C_1-C_4)$alkylphenyl group, a $(C_1-C_4)$alkoxyphenyl group, a $(C_1-C_4)$alkylthiophenyl group, a $(C_1-C_4)$alkylsulfonylphenyl group or a $(C_1-C_4)$alkylsulfonyl-bromophenyl group;

$R^3$ denotes a ($C_1$–$C_4$)alkyl group, a ($C_2$–$C_4$)alkenyl group, a ($C_1$–$C_4$)alkoxy-($C_1$–$C_4$)alkyl group, a methylthio($C_1$–$C_4$)alkyl group, a cyclohexyl group, a cyclopentyl group, a cyclopentyl-($C_1$–$C_4$)alkyl group, a benzyl group, a chlorobenzyl group, a fluorobenzyl group, a cyanobenzyl group, a dichlorobenzyl group, a chlorobromobenzyl group, a chlorofluorobenzyl group, a chlorocyanobenzyl group, a mono- or di-($C_1$–$C_4$)alkylbenzyl group, a ($C_1$–$C_4$)alkoxybenzyl group, a ($C_1$–$C_4$)alkylchlorobenzyl group, a ($C_1$–$C_4$)alkylthiobenzyl group, a methylsulfonylbenzyl group, a phenylethyl group, a methyldichlorophenylethyl group, a 1-chlorophenyl-propyl group, a phenyl group, a chlorophenyl group, a dichlorophenyl group, a dichlorofluorophenyl group, or a ($C_2$–$C_4$)alkynyl group;

Z' is a linear ($C_1$–$C_3$)alkylene group; and

B is a hydrogen atom or a ($C_1$–$C_4$)alkyl group, and a salt of said 1,2,4-triazole derivative.

10. A 1,2,4-triazole derivative as claimed in claim 1 which is:

the compound of the formula

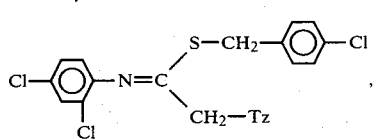

(Compound No. 123)

the compound of the formula

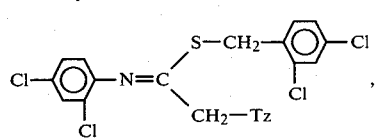

(Compound No. 129)

the compound of the formula

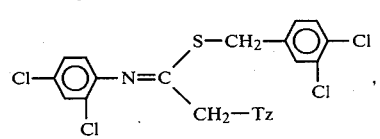

(Compound No. 131)

the compound of the formula

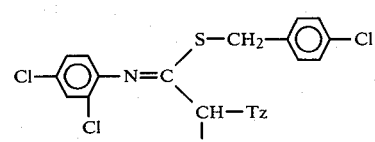

(Compound No. 142)

the compound of the formula

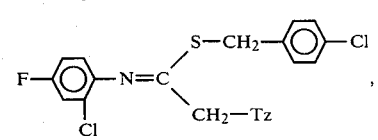

(Compound No. 204)

the compound of the formula

—continued

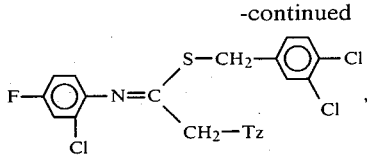

(Compound No. 210)

the compound of the formula

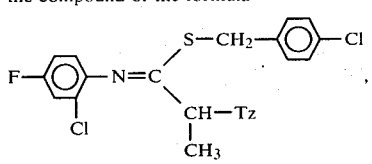

(Compound No. 214)

the compound of the formula

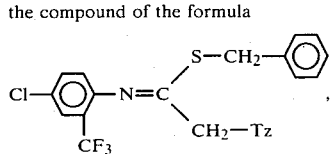

(Compound No. 279)

the compound of the formula

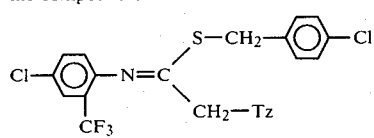

(Compound No. 280)

the compound of the formula

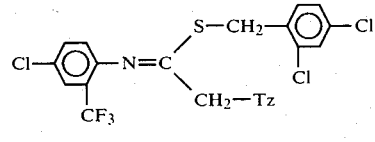

(Compound No. 284)

the compound of the formula

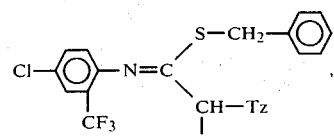

(Compound No. 292)

or the compound of the formula

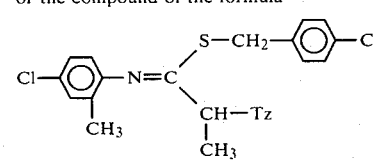

(Compound No. 293)

where each Tz denotes the 1,2,4-triazole-1-yl group of the formula

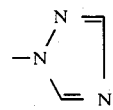

11. A fungicidal composition comprising as the active ingredient a fungicidally effective amount of a 1,2,4-triazole derivative as defined in claim 1, or a salt thereof, in association with an acceptable carrier for the active ingredient.

12. A method of combating the fungal pests of plants, which comprises treating plants, seeds or trees with a fungicidally effective amount of a 1,2,4-triazole derivative as defined in claim 1 or a salt thereof.

* * * * *